US008116544B2

(12) United States Patent
Masumoto

(10) Patent No.: US 8,116,544 B2
(45) Date of Patent: Feb. 14, 2012

(54) APPARATUS, METHOD, AND PROGRAM FOR DETECTING THREE DIMENSIONAL ABDOMINAL CAVITY REGIONS

(75) Inventor: Jun Masumoto, Ichiawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/736,396

(22) PCT Filed: Feb. 19, 2009

(86) PCT No.: PCT/JP2009/000718
§ 371 (c)(1),
(2), (4) Date: Mar. 18, 2011

(87) PCT Pub. No.: WO2009/122649
PCT Pub. Date: Oct. 8, 2009

(65) Prior Publication Data
US 2011/0164798 A1    Jul. 7, 2011

(30) Foreign Application Priority Data
Apr. 3, 2008 (JP) .................................. 2008-097630

(51) Int. Cl.
*G06K 9/00* (2006.01)
(52) U.S. Cl. .............................................. 382/128; 378/1
(58) Field of Classification Search .......... 382/128–132; 378/1–90
See application file for complete search history.

(56) References Cited

U.S. PATENT DOCUMENTS

| | | | | |
|---|---|---|---|---|
| 5,356,295 A * | 10/1994 | Grosz | ............................ | 434/267 |
| 5,835,619 A * | 11/1998 | Morimoto et al. | ............. | 382/132 |
| 6,701,174 B1 * | 3/2004 | Krause et al. | ................. | 600/407 |
| 8,001,974 B2 * | 8/2011 | Makower et al. | ............. | 128/898 |
| 8,002,465 B2 * | 8/2011 | Ahn | ............................... | 378/205 |
| 2003/0223627 A1 * | 12/2003 | Yoshida et al. | ............... | 382/128 |
| 2007/0106152 A1 * | 5/2007 | Kantrowitz et al. | .......... | 600/424 |

(Continued)

FOREIGN PATENT DOCUMENTS

JP        07-073291        3/1995

(Continued)

OTHER PUBLICATIONS

N. Murata et al., "Constructing a Diapgragm Model for Automated . . . ", IEICE Technical Report on Medical Imaging, Jan. 21, 2005, pp. 107-112,vol. 104, No. 579.

*Primary Examiner* — Manav Seth
(74) *Attorney, Agent, or Firm* — Jean C. Edwards, Esq.; Edwards Neils PLLC

(57) ABSTRACT

An apparatus is provided with: a bone region extracting section for extracting bone regions representing bones of a subject within a plurality of axial tomographic images obtained from a three dimensional image representing a portion of the subject from the vicinity of the upper end of the liver to the vicinity of the pubic symphysis; a bone boundary point detecting section for detecting a plurality of bone boundary points representing the boundaries between the detected bone regions and regions positioned toward the interiors of the bone regions within the plurality of axial tomographic images; and an abdominal cavity region extracting section for estimating curved surfaces within the three dimensional image that substantially contact the interiors of the plurality of bone boundary points detected in each of the plurality of axial tomographic images, and for extracting a region surrounded by the curved surfaces as a three dimensional abdominal cavity region.

11 Claims, 13 Drawing Sheets

U.S. PATENT DOCUMENTS

| | | | |
|---|---|---|---|
| 2007/0250020 A1* | 10/2007 | Kim et al. | 604/264 |
| 2008/0267471 A1* | 10/2008 | Yu et al. | 382/128 |
| 2009/0003677 A1* | 1/2009 | Wang | 382/131 |
| 2010/0128954 A1* | 5/2010 | Ostrovsky-Berman et al. | 382/131 |

FOREIGN PATENT DOCUMENTS

| | | |
|---|---|---|
| JP | 09-187444 | 7/1997 |
| JP | 2002-222410 | 8/2002 |
| JP | 2003-339694 | 12/2003 |
| JP | 2004-057275 | 2/2004 |
| JP | 2008-006188 | 1/2008 |
| JP | 2008-043565 | 2/2008 |
| WO | 2007/145093 | 12/2007 |
| WO | WO 2007/145093 A1 | 12/2007 |

* cited by examiner

APPARATUS, METHOD, AND PROGRAM FOR DETECTING THREE DIMENSIONAL ABDOMINAL CAVITY REGIONS

CROSS-REFERENCE TO RELATED APPLICATIONS

The present invention is a 35 USC 371 national stage entry of PCT/JP2009/000718, filed Feb. 19, 2009, which claims priority from Japanese Patent Application No. 2008-097630, filed Apr. 3, 2008, the contents of all of which are herein incorporated by reference in their entirety.

BACKGROUND OF THE INVENTION

1. Field of the Invention

The present invention is related to a three dimensional image analyzing process. Particularly, the present invention is related to an apparatus and a method for performing a process to detect abdominal cavity regions of subjects within three dimensional images, and to a program that causes a computer to execute the method.

2. Description of the Related Art

Amounts of body fat and body fat percentages are measured by detecting regions corresponding to CT values that represent fat within cross sectional images perpendicular to the axes of the bodies of subjects (axial cross sections) in the vicinity of the spleens of the subjects, imaged and obtained by CT. A technique has been proposed that separates the fat regions within the images into subcutaneous fat regions and visceral fat regions by an image analyzing process.

Specifically, methods have been proposed, in which an outline is tracked along the outer periphery of the surface of a subject's body within axial tomographic images obtained by CT, regions of interest on the surface of the body are extracted, and total fat regions are extracted from within the regions of interest on the surface of the body. Then, the total fat regions within the regions of interest on the surface of the body are removed, regions corresponding to the abdominal wall muscle layer are extracted, and the outlines of the abdominal wall muscles are tracked, to extract visceral regions of interest that surround visceral fat. Thereafter, the visceral fat regions are extracted from within the visceral regions of interest, and subcutaneous fat regions are extracted by subtracting the visceral fat regions from the total fat regions (refer to Patent Documents 1 and 2, for example). Generally, there are gaps within the abdominal wall muscle layer. These methods take these gaps into consideration when tracking the outlines of the abdominal wall muscles, and the outlines are tracked by rolling a small circle such that it contacts the outer periphery of the abdominal wall muscle layer.

In addition, another method for discriminating visceral fat regions from subcutaneous fat regions has been proposed (refer to Patent Document 3, for example). In this method, axial tomographic images of the abdomen obtained by CT are classified into skin/muscle pixel regions, fat pixel regions, and subject exterior regions. The skin/muscle pixel regions adjacent to the subject exterior pixel regions are replaced with the subject exterior pixel regions to remove the skin/muscle pixel regions that represent the skin on the surface of the body. Then, the skin/muscle pixel regions that remain after removal are expanded such that the skin/muscle pixel regions that represent the abdominal wall muscle and the peritoneal membrane completely surround the fat pixel regions that correspond to visceral fat. Thereafter, the fat pixel regions adjacent to the subject exterior pixel regions and components linked to these pixel regions are labeled. The labeled regions are expanded toward the interior for an amount corresponding to the amount of expansion of the aforementioned skin/muscle pixel regions, and designated as subcutaneous fat regions. The fat pixel regions within the images other than the subcutaneous fat regions are designated as visceral fat. Further, Patent Document 3 discloses that the aforementioned method may be performed with respect to a plurality of axial tomographic images of the abdomen, the area of the subcutaneous fat region and the visceral fat region of each of the each image may be multiplied by the slice thickness of the image, and the sum of the multiplication results for each image may be calculated, to derive the volume of the subcutaneous fat and the visceral fat within the entirety of the abdomen.

Patent Document 1:
Japanese Unexamined Patent Publication No. 2002-222410
Patent Document 2:
Japanese Unexamined Patent Publication No. 2004-057275
Patent Document 3:
Japanese Unexamined Patent Publication No. 2003-339694

In the case that the axial image illustrated in FIG. 14A is employed to measure subcutaneous fat and visceral fat, for example, a fat region within a region $Rgn_1$ within the abdominal cavity covered by the peritoneal membrane should be designated as visceral fat, and a fat region within a region $Rgn_2$ between the surface of the body and the outer periphery of the abdominal wall muscle should be designated as subcutaneous fat. However, a fat region within a region $Rgn_3$ between the outline of the abdominal cavity and the outer periphery of the abdominal wall muscle in the vicinity of the area behind the spinal column should not be designated as either subcutaneous fat or visceral fat. FIG. 14B illustrates examples of a visceral fat region $Rgn_{1f}$ and a subcutaneous fat region $Rgn_{2f}$ to be extracted at the vicinity of the upper edge of the abdominal cavity, FIG. 14C illustrates examples of a visceral fat region $Rgn_{1f}$ and a subcutaneous fat region $Rgn_{2f}$ to be extracted at the vicinity of the center of the abdominal cavity, and FIG. 14D illustrates examples of a visceral fat region $Rgn_{1f}$ and a subcutaneous fat region $Rgn_{2f}$ to be extracted at the vicinity of the lower edge of the abdominal cavity.

However, in the methods disclosed in the aforementioned patent documents, the outer periphery of the abdominal wall muscle to the exterior of the peritoneal membrane is used as a reference, and all fat regions toward the interior thereof are judged to be visceral fat. Therefore, the fat regions within the regions $Rgn_3$ of FIG. 14 will be erroneously judged to be visceral fat. Fat regions are often observed in the vicinities of areas behind the spinal column in axial tomographic images in the vicinity of the pelvis. Therefore, if the volume of body fat is measured three dimensionally by calculating the sum of measurement results obtained from a plurality of axial tomographic images of the abdominal region, the erroneous judgments will cause the amount of errors to become great.

Meanwhile, in the case that body fat is measured using only axial tomographic images in the vicinity of a subject's spleen, the states of structures within the subject included in the images will vary due to the influence of the subject's respiration and the like. Therefore, it is not necessarily the case that accurate measurement can be performed. Accordingly, the method for measuring body fat three dimensionally by calculating the sum of measurement results obtained from a plurality of axial tomographic images as disclosed in Patent Document 3 is effective for such cases.

However, the method that defines the boundaries between subcutaneous fat and visceral fat by expanding the skin/muscle pixel regions that represent the abdominal wall muscle and the peritoneal membrane disclosed in Patent Document 3 assumes that the visceral fat region is surrounded by the abdominal wall muscle. Therefore, although a certain degree of accuracy in definition can be expected in axial tomographic images in the vicinity of the spleen, the assumption fails in axial tomographic images in the vicinity of the pelvis. Accordingly, the boundaries between subcutaneous fat and visceral fat cannot be accurately defined in these images.

As described above, there is demand to more accurately detect the abdominal cavity regions of subjects, in order to discriminate between subcutaneous fat regions and visceral fat regions, to more accurately measure the body fat of subjects.

The present invention has been developed in view of the foregoing circumstances. It is an object of the preset invention to provide an apparatus, method, and a program for detecting three dimensional abdominal cavity regions that realize more highly accurate three dimensional detection of the abdominal cavity regions of subjects.

SUMMARY OF THE INVENTION

A three dimensional abdominal cavity region extracting apparatus of the present invention is characterized by comprising:

bone region extracting means, for extracting bone regions that represent the bones of a subject within a plurality of axial tomographic images obtained from a three dimensional image that represents a portion of the subject from the vicinity of the upper end of the liver to the vicinity of the pubic symphysis;

bone boundary point detecting means, for detecting a plurality of bone boundary points that represent the boundaries between the detected bone regions and regions positioned toward the interiors of the bone regions within the plurality of axial tomographic images; and abdominal cavity region extracting means, for estimating curved surfaces within the three dimensional image that substantially contact the interiors of the plurality of bone boundary points detected in each of the plurality of axial tomographic images, and for extracting a region surrounded by the curved surfaces as a three dimensional abdominal cavity region.

A three dimensional abdominal cavity region extracting method of the present invention is characterized by comprising the steps of:

extracting bone regions that represent the bones of a subject within a plurality of axial tomographic images obtained from a three dimensional image that represents a portion of the subject from the vicinity of the upper end of the liver to the vicinity of the pubic symphysis;

detecting a plurality of bone boundary points that represent the boundaries between the detected bone regions and regions positioned toward the interiors of the bone regions within the plurality of axial tomographic images; and estimating curved surfaces within the three dimensional image that substantially contact the interiors of the plurality of bone boundary points detected in each of the plurality of axial tomographic images; and extracting a region surrounded by the curved surfaces as a three dimensional abdominal cavity region.

A three dimensional abdominal cavity region extracting program of the present invention causes a computer to execute the above method.

Hereinafter, the details of the present invention will be described.

A human body is a specific example of the "subject".

Image data that represent the "three dimensional image" may be constructed by a conglomeration of image data that represent the "plurality of axial tomographic images". Alternatively, the image data that represent the "three dimensional image" may be image data based on a multi dimensional coordinate system, such as voxel data. In the latter case, the "plurality of axial tomographic images" are obtained by reconstructing processes based on the image data that represent the three dimensional image.

A specific example of a method for detecting the bone boundary points is that in which search reference lines having end points at both sides of a line that bisects the subject in the horizontal direction are set at positions which are clearly anatomically in the abdominal cavity region within each of the plurality of axial tomographic images, such that the distances between the end points become shorter in axial tomographic images that represent lower portions of the subject, searches are performed along a plurality of lines of sight that do not intersect and extend from a plurality of points along the search reference lines toward the exterior of the subject, and points that contact the bone regions first are detected as the bone boundary points. Here, the two end points of the search reference lines may be the same point at the lower portions of the subject.

Specific examples of methods for "estimating curved surfaces within the three dimensional image that substantially contact the interiors of the plurality of bone boundary points" include that in which predetermined interpolating calculations are performed with respect to a plurality of bone boundary points, that in which shape models of curved surfaces obtained by statistical analysis of main component analysis are prepared in advance and a plurality of bone boundary points are fitted into the shape models, and that in which a multidimensional function that can approximate a plurality of bone boundary points is estimated.

Here, the expression "substantially contact the interiors" includes cases in which the plurality of bone boundary points are contact points with the estimated curved surfaces, and cases in which the plurality of bone boundary points are equivalent to being in contact with the estimated curved surfaces. A specific example of the latter case is that in which the estimated curved surfaces and curved surfaces that pass through the plurality of bone boundary point are similar in shape, the estimated curved surfaces are more toward the interior of the subject than the curved surfaces that pass through the plurality of bone boundary points, and the distances between corresponding points in the two sets of curved surfaces are minute (approximately 1 mm to 5 mm, for example).

A configuration may be adopted, wherein: the outline of the surface of the body of the subject is extracted from each of the plurality of axial tomographic images; and the curved surfaces are estimated such that the curved surfaces do not extend outside the exterior of the surface of the body.

Further, a configuration may be adopted, wherein: the outline of the exterior of the abdominal wall muscles of the subject is extracted from within each of the plurality of axial tomographic images; and the curved surfaces are estimated such that the curved surfaces do not extend outside the outline of the exterior of the abdominal wall muscles.

Note that here, the curved surfaces may be estimated in a single step process, based on the bone boundary points and the outline of the surface of the body and/or the outline of the exterior of the abdominal wall muscles. Alternatively, the curved surfaces may be estimated in a multiple step process, first based on the bone boundary points, and then based on the outline of the surface of the body and/or the outline of the exterior of the abdominal wall muscles.

A configuration may be adopted, wherein: diaphragm portions are extracted from each of the plurality of axial tomographic images and/or each of a plurality of axial tomographic images obtained from a three dimensional image that represents the thoracic region of the subject; and a region from within the three dimensional image surrounded by the extracted diaphragm portions and the curved surfaces is extracted as the three dimensional abdominal cavity region. In addition, a three dimensional abdominal cavity region may be extracted in a single step process, by estimating the curved surfaces based on both data regarding the diaphragm portions and data regarding the bone boundary points.

A configuration may be adopted, wherein: regions having pixel values that correspond to fat of the subject within the extracted three dimensional abdominal cavity region are discriminated as three dimensional visceral fat regions.

A configuration may be adopted, wherein: subcutaneous fat regions that represent subcutaneous fat of the subject are discriminated from within each of the plurality of axial tomographic images, to discriminate three dimensional subcutaneous fat regions within the three dimensional image.

According to the present invention, bone regions are detected within a plurality of axial tomographic images obtained from a three dimensional image that represents a portion of the subject from the vicinity of the upper end of the liver to the vicinity of the pubic symphysis; a plurality of bone boundary points that represent the boundaries between the detected bone regions and regions positioned toward the interiors of the bone regions are detected within the plurality of axial tomographic images; and curved surfaces within the three dimensional image that substantially contact the interiors of the plurality of bone boundary points detected in each of the plurality of axial tomographic images are estimated; and a region surrounded by the curved surfaces is extracted as a three dimensional abdominal cavity region.

Here, the estimated curved surfaces substantially contact the interiors of the plurality of bone boundary points that represent the boundaries between the bone regions and regions positions toward the interiors of the bone regions within the subject. Therefore, the curved surfaces are positioned toward the interior of the spinal column in the vicinity of the spinal column within the axial tomographic images. Accordingly, the regions $Rgn_3$ between the outline of the abdominal cavity and the outer periphery of the abdominal wall muscle in the vicinity of the area behind the spinal column are outside the abdominal cavity region, and the extraction accuracy of the abdominal cavity region is improved. In the case visceral fat is measured, for example, the regions $Rgn_3$ are removed from the visceral fat regions, and therefore, the accuracy of fat region discrimination is improved.

In addition, the plurality of bone boundary points within the plurality of axial tomographic images are utilized three dimensionally to estimate the curved surfaces to extract the three dimensional abdominal cavity region. Therefore, the estimation accuracy of the curved surfaces is higher compared to the method disclosed in Patent Document 3, in which the regions are discriminated independently for each axial tomographic image, because data regarding the bone boundary points in the axial direction of the body are also utilized. As a result, the accuracy of abdominal cavity region extraction is also improved.

A configuration may be adopted, in which the diaphragm portion of the subject is extracted, and a region within the three dimensional image surrounded by the extracted diaphragm portion and the curved surfaces is extracted as the three dimensional abdominal cavity region. In this case, the extraction accuracy with respect to the upper edge portion of the abdominal cavity is improved.

Configurations may be adopted, in which the outline of the surface of the subject's body or the outline of the exterior of the abdominal wall muscles are extracted, and the curved surfaces are estimated such that they do not extend outside the extracted outlines. In these cases, the curved surfaces being estimated as shapes that protrude outside of these outlines in portions of the subject in the vicinity of the abdomen where no ribs or pelvis are present can be avoided. Therefore, the accuracy of estimation of the curved surfaces in the vicinity of the abdomen is improved. As a result, accuracy of abdominal cavity region extraction is improved in the vicinity of the abdomen.

In addition, a configuration may be adopted, wherein: reference lines having endpoints at both sides of a line that bisects the subject in the horizontal direction are set at positions which are clearly anatomically in the abdominal cavity region within each of the plurality of axial tomographic images, such that the distances between the end points become shorter in axial tomographic images that represent lower portions of the subject, searches are performed along a plurality of lines of sight that do not intersect and extend from a plurality of points along the search reference lines toward the exterior of the subject, and points that contact the bone regions first are detected as the bone boundary points. In this case, the initiation points of the searches include those which are shifted from the center of the subject in the horizontal direction. Therefore, it becomes possible to set the bone boundary points along the interiors of the spinal column (vertebrae) positioned at the center. In addition, the search reference lines are set such that the distances between the end points become shorter in axial tomographic images that represent lower portions of the subject. Therefore, the search initiation points can be set within the interior of the pelvis in axial tomographic images in the vicinity of the pelvis. This enables setting of the bone boundary points within the interior of the pelvis, which contributes to improvements in the accuracy of estimation of the curved surfaces.

DESCRIPTION OF THE PREFERRED EMBODIMENTS

Hereinafter, a three dimensional body fat measuring system in which a three dimensional abdominal cavity region extracting apparatus of an embodiment of the present invention is incorporated will be described with reference to the attached drawings.

Figure 1:
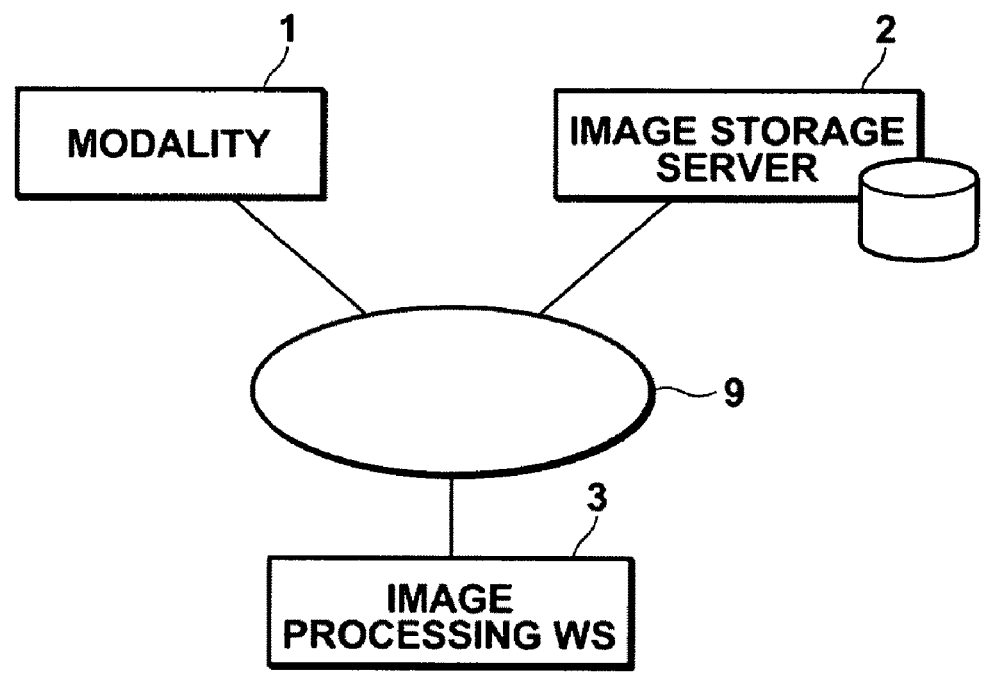
FIG. 1 is a schematic diagram that illustrates the three dimensional body fat measuring system, in which the three dimensional abdominal cavity region extracting process according to an embodiment of the present invention is incorporated.

FIG. 1 is a diagram that illustrates the hardware structure of a medical image information display apparatus according to a first embodiment of the present invention. As illustrated in FIG. 1, the system includes: a modality 1; an image storage server 2; and an image processing workstation 3. The modality 1, the image storage server 2, and the image processing workstation 3 are connected via a network 9 such that they can communicate with each other.

The modality 1 obtains three dimensional medical images (voxel data) V that represent subjects. Specifically, the modality 1 is a CT apparatus, an MRI apparatus, an ultrasound apparatus, or the like. In the present embodiment, the three dimensional images V are constituted by image data which are conglomerations of axial tomographic images obtained by a CT apparatus.

The image storage server 2 is a computer that stores and manages the medical images V obtained by the modality 1 and medical image data which are generated by image processes at the image processing workstation 3. The image storage server 2 is equipped with a high capacity external storage device and database management software (for example, ORDB (Object Relational Database) management software).

The image processing workstation 3 is a computer that administers image processes onto three dimensional medical images V obtained by the modality 1 and three dimensional medical images V obtained from the image storage server 2 in response to requests by diagnosticians, and displays the processed images. The image processing workstation 3 is equipped with: input devices, such as a keyboard and a mouse, for inputting requests from diagnosticians; a main memory device of a capacity capable of storing the obtained three dimensional medical images V; and a display for displaying generated images. A three dimensional body fat measuring process that includes a three dimensional abdominal cavity region extracting process of the present invention is loaded into the image processing workstation 3. This process is realized by executing a program which is installed from a storage medium such as a CD-ROM. Alternatively, the program may be downloaded from a server connected to the image processing workstation 3 via a network such as the Internet, and then installed.

The storage format and communications among each component via the network 9 are based on a protocol, such as the DICOM (Digital Imaging and Communications in Medicine) protocol.

Figure 2:
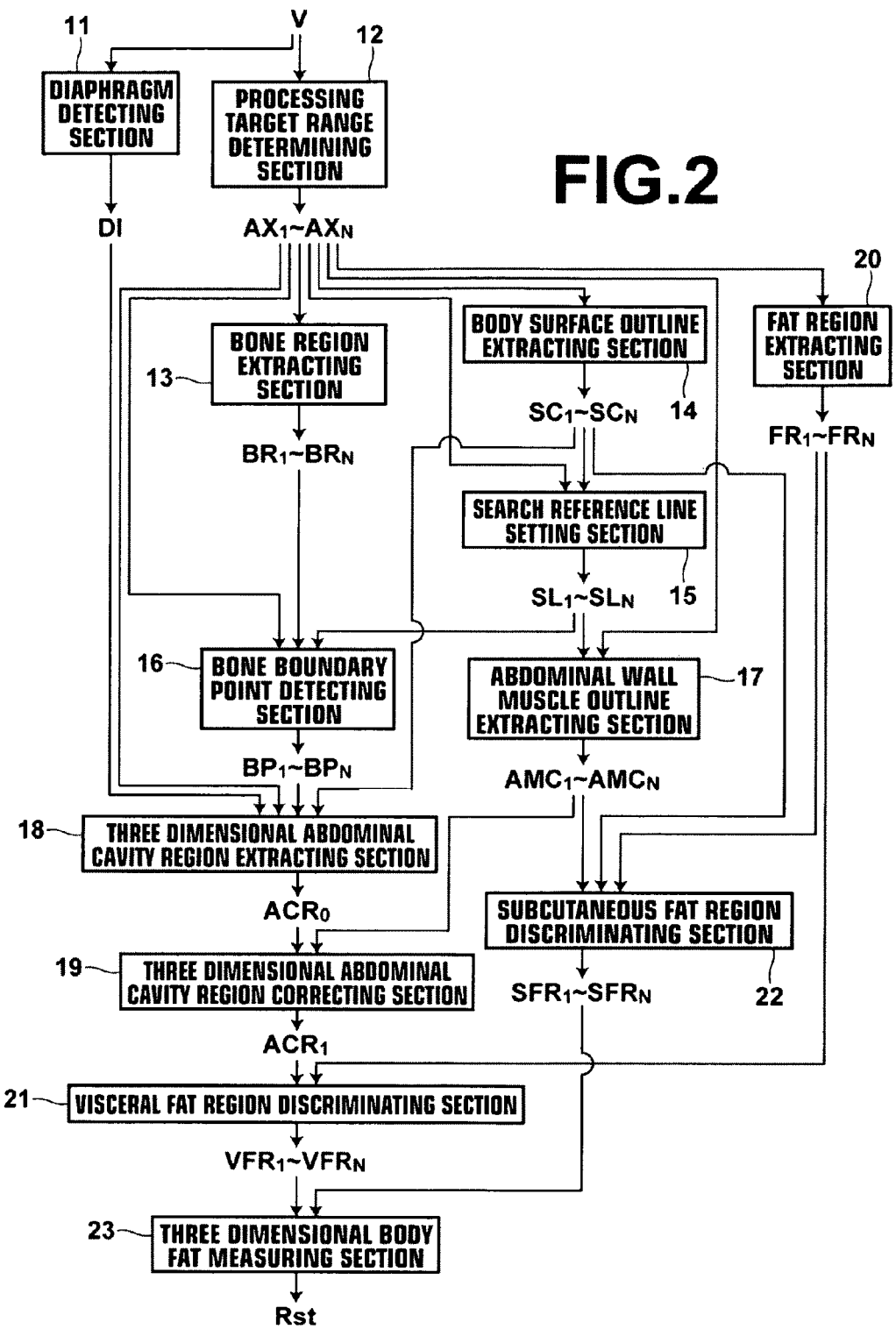
FIG. 2 is a block diagram that schematically illustrates the structures and flow of processes that realize the three dimensional body fat measuring function of the embodiment of the present invention.

FIG. 2 is a block diagram that illustrates portions of the image processing workstation 3 related to the three dimensional body fat measuring process that includes the three dimensional abdominal cavity region extracting process of the present invention. As illustrated in FIG. 2, the three dimensional body fat measuring process that includes the three dimensional abdominal cavity region extracting process of the present invention is realized by: a diaphragm detecting section 11; a processing target range determining section 12; a bone region extracting section 13; a body surface outline extracting section 14; a search reference line setting section 15; a bone boundary point detecting section 16; an abdominal wall muscle outline extracting section 17; a three dimensional abdominal cavity region extracting section 18; a three dimensional abdominal cavity correcting section 19; a fat region extracting section 20; a visceral fat region discriminating section 21; a subcutaneous fat region discriminating section 22; and a three dimensional body fat measuring section 23. Hereinafter, the details of each processing section will be described.

Figure 3:
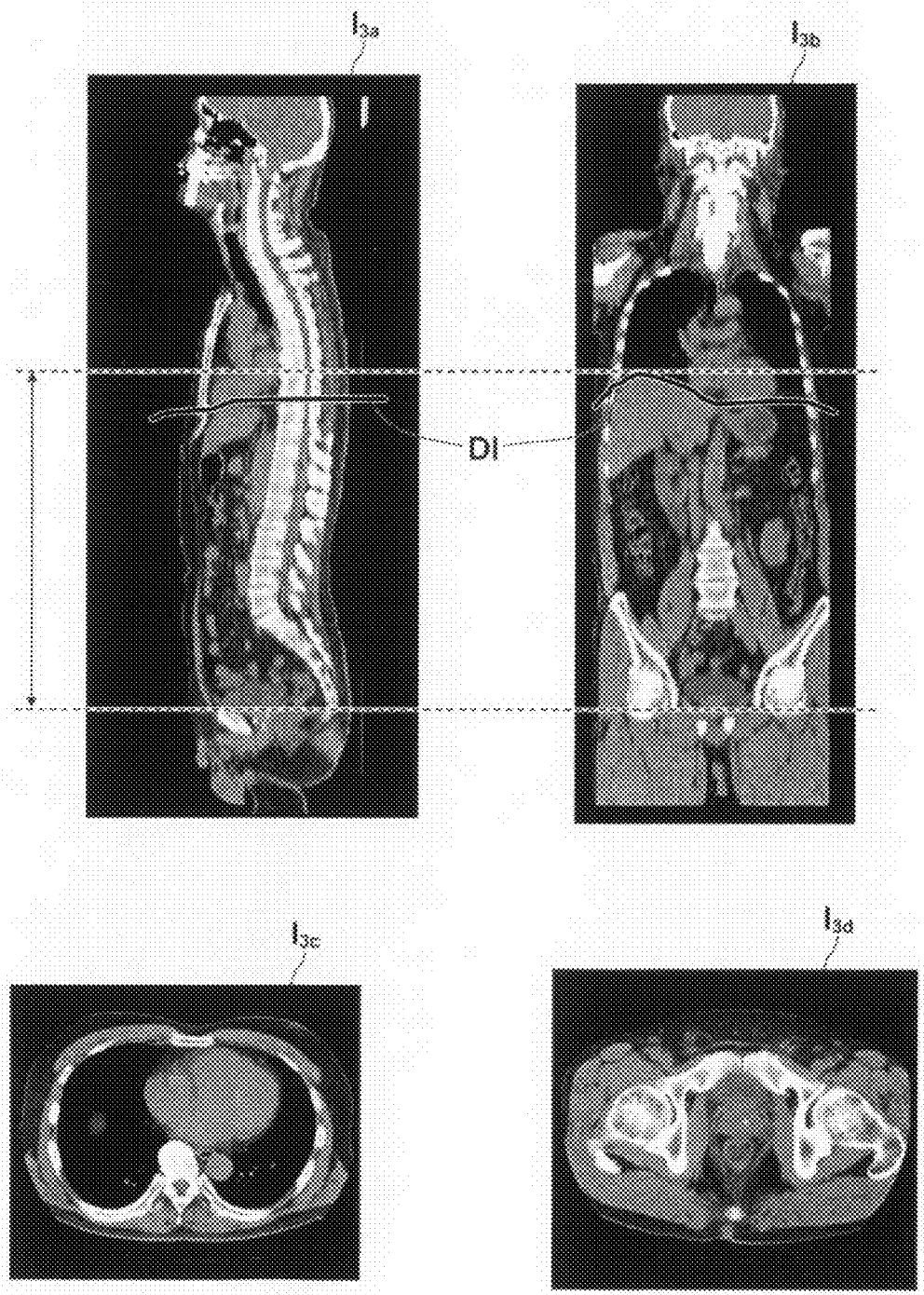
FIG. 3 is a collection of diagrams that illustrate an example of detection results for the diaphragm and examples of axial tomographic images within a processing target range.

The diaphragm detecting section 11 detects a curved surface DI that represents the diaphragm from the three dimensional medical image data V. Any method which is known when the present invention is to be executed may be employed as the detecting method. Examples of such known methods for detecting the curved surface DI that represents the diaphragm include that in which axial tomographic images toward the side of the thorax from among the three dimensional medical image data V are employed as inputs, regions having pixel values corresponding to CT values for air are extracted as lung fields, and the boundary at the lower end of the extracted lung field regions are approximated by a function, or by fitting into statistical models that represent shapes and outlines (for details, refer to N. Murata, et al., "Constructing a Diaphragm Model for Automated Segmentation from Torso CT Images", IEICE Technical Report on Medical Imaging, Vol. 104, No. 579, pp. 107-112, The Institute of Electronics, Information and Communication Engineers, Jan. 21, 2005). The sagittal tomographic image $I_{3a}$ and the coronal tomographic image $I_{3b}$ of FIG. 3 represent an example of a detected diaphragm DI.

The processing target range determining section 12 determines axial tomographic images $AX_1$ through $AX_N$ that represent portions from the vicinity of the upper edge of the liver to the vicinity of the pubic symphysis from among the three dimensional medical image data V, which are to be targets of the three dimensional abdominal cavity region extracting process. Here, the numerals 1 through N distinguish each axial tomographic image, and in the present embodiment, N is the number of axial tomographic images which are processing targets. The arrow and dotted lines within the sagittal tomographic image $I_{3a}$ and the coronal tomographic image $I_{3b}$ of FIG. 3 represent the range of axial tomographic images $AX_1$ through $AX_N$, which are processing targets. The axial tomographic images $AX_1$ through $AX_N$ may be determined manually by the following methods. The sagittal image tomographic image $I_{3a}$ or the coronal tomographic image $I_{3b}$ of FIG. 3 is displayed on a screen, and a user interface may prompt a user to specify an axial tomographic image $AX_1$ (in the vicinity of the upper edge of the liver, indicated by the upper dotted line) and an axial tomographic image $AX_N$ (in the vicinity of the pubic symphysis, indicated by the lower dotted line) by operating the mouse. Alternatively, the user interface may sequentially display axial tomographic images of the subject while moving the slice positions, and receive specification of a starting point and an end point of the processing target range by the user operating the mouse, when an axial tomographic image in the vicinity of the upper edge of the liver (the axial tomographic image $AX_1$ of FIG. 3) and an axial tomographic image in the vicinity of the pubic symphysis (axial tomographic image $AX_N$ of FIG. 3) are displayed. As a further alternative, an axial tomographic image $AX_1$ (in the vicinity of the upper edge of the liver, indicated by the upper dotted line) and an axial tomographic image $AX_N$ (in the vicinity of the pubic symphysis) may be automatically determined employing an image discriminating process. For example, the portion discriminating process proposed in Japanese Patent Application No. 2007-104846 may be applied. That is, classifiers are generated with respect to axial tomographic images of the vicinity of the upper edge of the liver and axial tomographic images of the vicinity of the pubic symphysis, by performing learning based on the AdaBoost method employing a plurality of types of features such as the percentage of air and bone within images, calculated from a plurality of learning sample images which are known to represent the aforementioned portions, and a plurality of sample images which are known not to represent the aforementioned portions. The same features are calculated from each axial tomographic image which is a target of judgment, and the features calculated from each image are input to the classifiers fro each portions, to obtain scores that represent the likelihood that the images represent the aforementioned portions.

The axial tomographic images that have the highest scores for each portion can be automatically determined to be the starting point and the end point of the processing target range. As still another alternative, a portion discriminating process that does not employ the classifiers generated by the aforementioned learning process may be executed. In this alternate portion discriminating process, score tables that define the relationships among the features and the scores may be generated experimentally/empirically/statistically. The scores may be calculated with respect to the features which are calculated from each axial tomographic image which is a target of judgment from the score tables.

The bone region extracting section 13 extracts regions having pixel values corresponding to CT values for bones as bone regions $BR_1$ through $BR_N$, from within the axial tomographic images $AX_1$ through $AX_N$.

The body surface outline extracting section 14 extracts body surface outlines $SC_1$ through $SC_N$ from within the axial tomographic images $AX_1$ through $AX_N$. Any method which is known when the present invention is to be executed may be employed as the extracting method. An example of such a known method is that in which the axial tomographic images $AX_1$ through $AX_N$ are binarized, and then the body surface outlines $SC_1$ through $SC_N$ are extracted by an outline extracting process (for details, refer to Japanese Unexamined Patent Publication No. H9 (1997)-187444).

Figure 4:
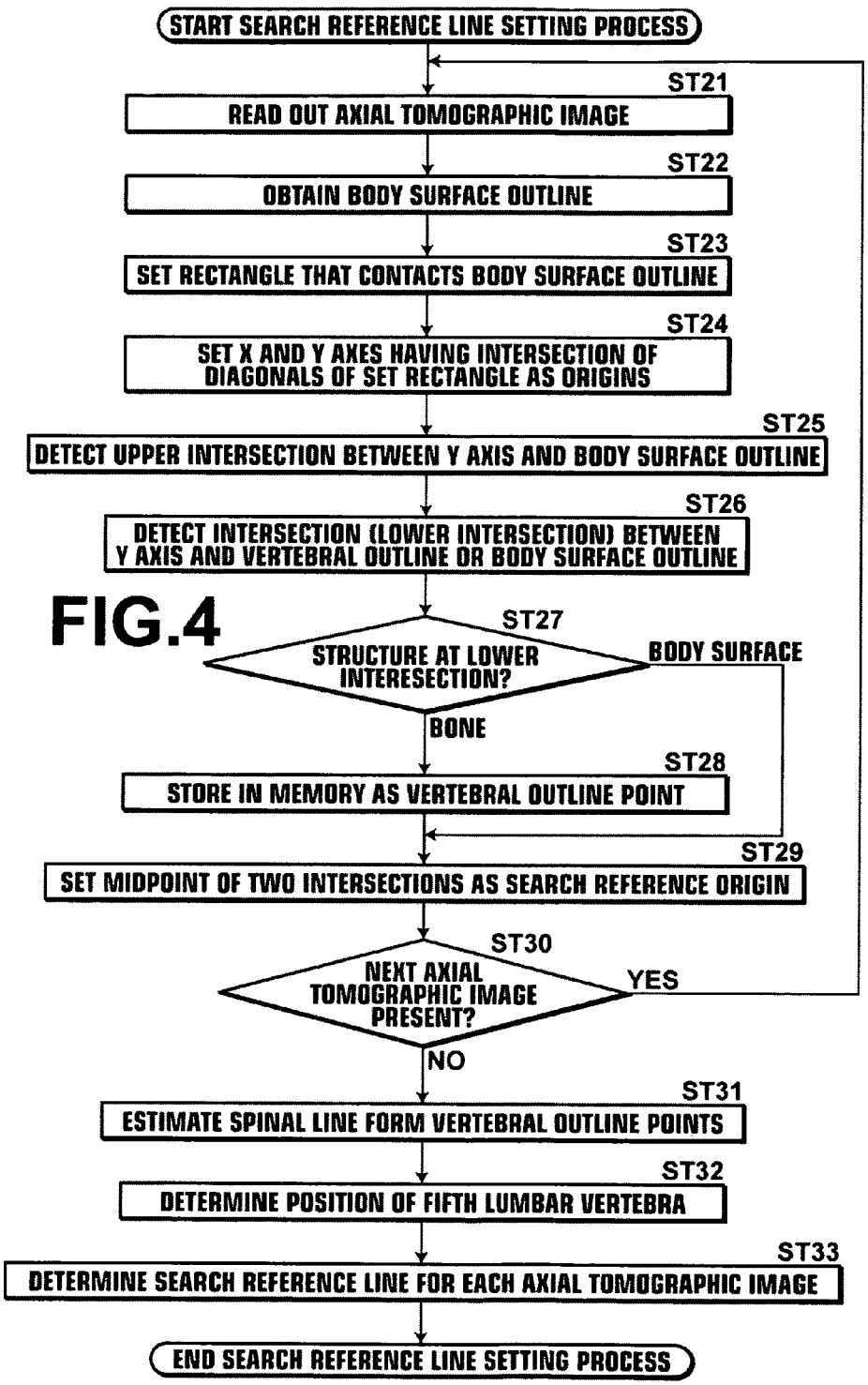
FIG. 4 is a flow chart that illustrates the steps of the search reference line setting process.
Figure 5:
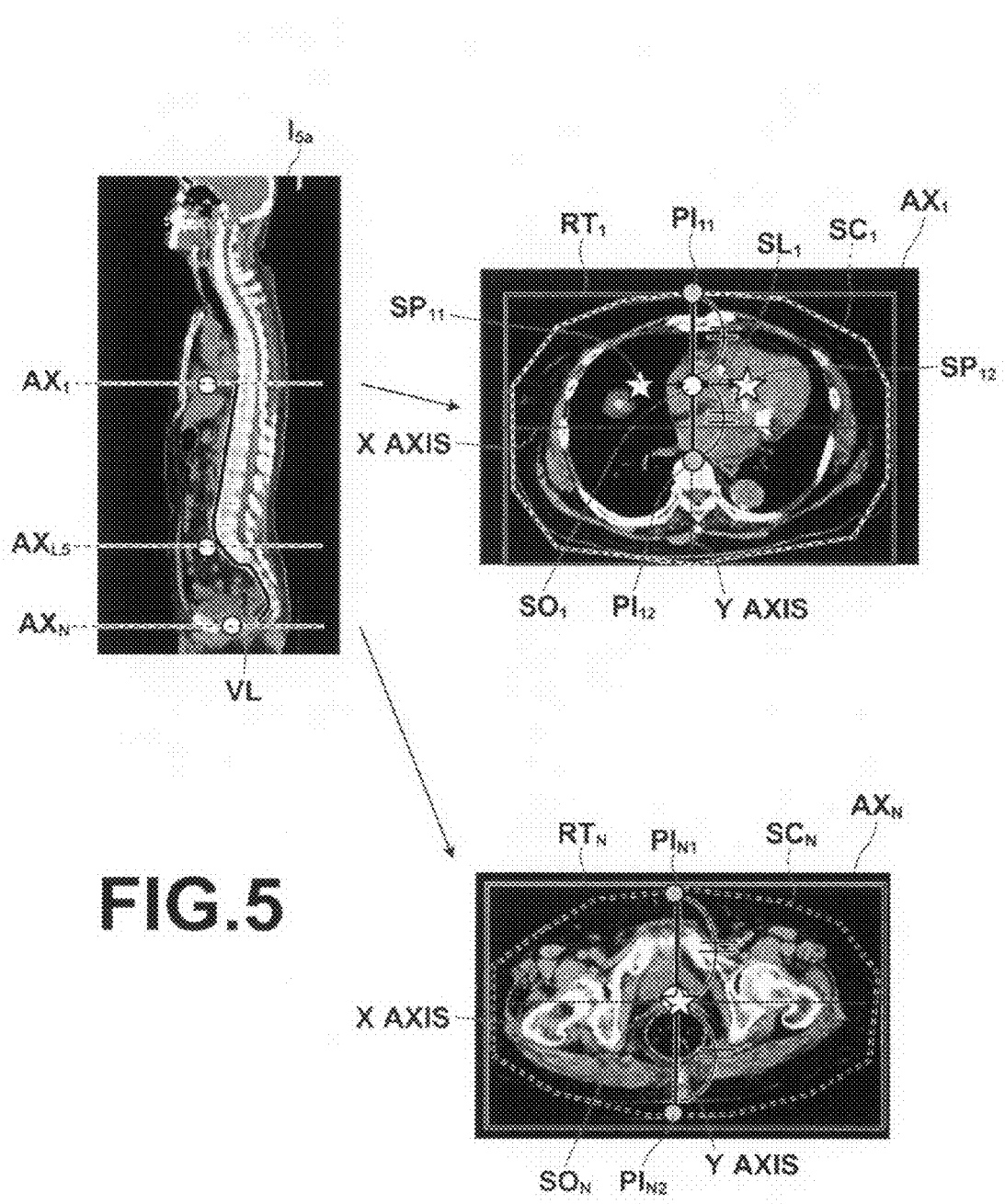
FIG. 5 is a collection of diagrams that illustrates an example of the setting method for search reference lines.

The search reference line setting section 15 sets search reference lines $SL_1$ through $SL_N$, which will be references for processes for extracting bone boundary points and the outlines of the exteriors of abdominal wall muscles to be described later. FIG. 4 is a flow chart that illustrates an example of a specific setting method. In addition, the sagittal image $I_{5a}$ of FIG. 5 is obtained from the three dimensional medical image data V, and indicates the slice positions of several axial tomographic images with dotted lines. Further, FIG. 5 schematically illustrates setting methods for search reference lines with respect to axial tomographic images $AX_1$ and $AX_N$ in the vicinities of the upper edge of the liver and the pubic symphysis.

First, the search reference line setting section 15 reads out the axial tomographic image $AX_1$ (step #21), obtains data regarding the body surface outline $SC_1$ extracted by the body surface outline extracting section 14 (step #22), sets a rectangle $RT_1$, the exterior of which contacts the body surface outline $SC_1$ (step #23), and sets X and Y axes having the intersection of the diagonals of the rectangle $RT_1$ as their origins (step #24). Next, an upper intersection $PI_{11}$ between the Y axis and the body surface outline $SC_1$ is detected, by searching along the Y axis from the origin toward the front of the subject (step #25). Further, a lower intersection $PI_{12}$ between the Y axis and the body surface outline $SC_1$ or a point having a pixel value corresponding to a bone CT value is detected, by searching along the Y axis from the origin toward the back of the subject, by judging whether search points have pixel values corresponding to bone CT values, and judging whether search points are a point along the body surface outline $SC_1$ (step #26). Here, because a vertebra is present within the axial tomographic image $AX_1$, the lower intersection $PI_{12}$ is a point having a pixel value that corresponds to a bone CT value. Accordingly, the search reference line setting section 15 judges that the structure at the lower intersection $PI_{12}$ is a bone (step #27: BONE), and stores the point as the most forward point of the outline of the vertebra within the subject (hereinafter, referred to as "vertebral outline point") in a predetermined memory region (step #28). Then, the midpoint $SO_1$ between the two intersections $PI_{11}$ and $PI_{12}$ is set as a search reference origin point (step #29).

The search reference line setting section 15 repeatedly performs the processes of steps #21 through #29 with respect to all of the remaining axial tomographic images $AX_2$ through $AX_N$ (step #30: YES), and obtains search reference origin points $SO_2$ through $SO_N$. The image at the lower right of FIG. 5 represents the setting results for the search reference origin point $SO_N$, which is set within the axial tomographic image $AX_N$ in which a vertebra is not present. As illustrated in FIG. 5, in the case that a vertebra is not present within an image, the intersection between the Y axis and the body surface outline $SC_N$ becomes the lower intersection $PI_{N2}$, the process of step #28 is skipped (step #27: BODY SURFACE), and the search reference origin point $SO_N$ becomes the midpoint between the two intersections of the Y axis and the body surface outline $SC_N$.

Next, after the search reference origin points $SO_1$ through $SO_N$ have been set for all of the processing target axial tomographic images $AX_1$ through $AX_N$ (step #30: NO), the search reference line setting section 15 approximates the data regarding the vertebral outline points stored in the predetermined memory region, that is, group of discrete points that represent the most forward points of the outline of the vertebrae within the subject, with a predetermined continuous function, to extract a vertebral line (VL in sagittal image $I_{5a}$ of FIG. 5) (step #31). Then, a slice position $AX_{L5}$ at which the vertebral line VL bends rapidly when viewed from the sagittal direction is obtained (step #32). Anatomically, this position is the position of the fifth lumbar vertebra.

Finally, the search reference line setting section 15 sets two points $SP_{11}$ and $SP_{12}$ through $SP_{N1}$ and $SP_{N2}$ (hereinafter, referred to as "search reference end points") within each axial tomographic image $AX_1$ through $AX_N$ which are positioned at either side of the Y axis and are separated from the search reference origin points $SO_1$ through $SO_N$ for predetermined distances in the direction of the X axis (the horizontal direction of the subject), and determines line segments that connect the search reference end points within each axial tomographic image $AX_1$ through $AX_N$ as search reference lines $SL_1$ through $SL_N$.

Figure 6:
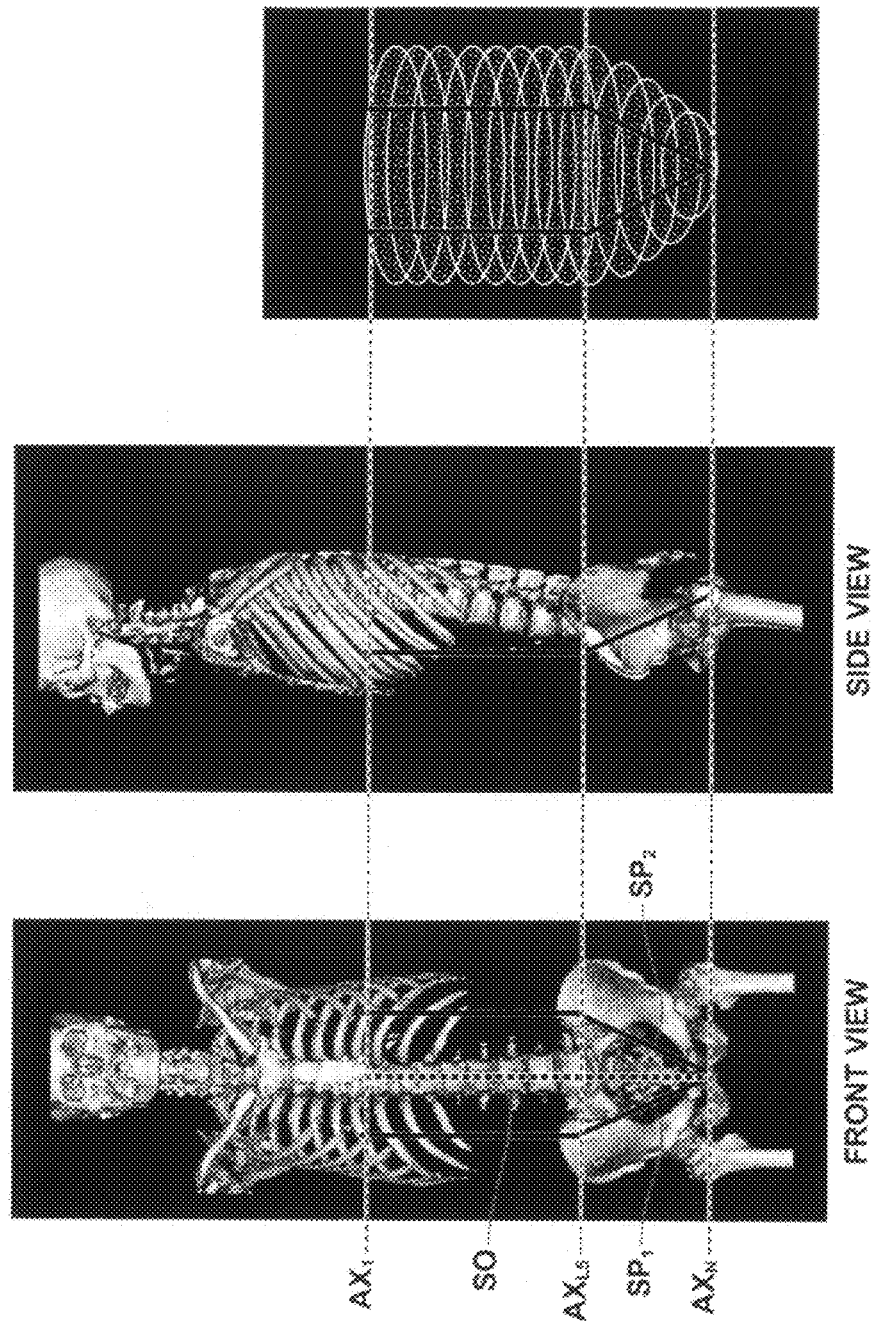
FIG. 6 is a collection of diagrams that represent the positions of the search reference end points within a coronal tomographic image and a sagittal tomographic image, and a shape model in which a reference coordinate system for the abdominal cavity region is defined.

Here, the distances between the search reference end points are set at a predetermined distance, which has been obtained statistically/empirically in advance such that both of the two search reference endpoints are included within the abdominal cavity region, from the axial tomographic image $AX_1$ at the vicinity of the upper edge of the liver to the axial tomographic image $AX_{L5}$ at the fifth lumbar vertebra. In axial tomographic images that represent slice positions below the fifth lumbar vertebra, the distances between the search reference endpoints are set such that they become smaller at lower axial tomographic images, and such that the search reference end points converge to a single point (such that the distance becomes 0) in the axial tomographic image $AX_N$ at the vicinity of the pubic symphysis. The image at the left of FIG. 6 illustrates the search reference end points which have been set in this manner within a coronal tomographic image. The image at the center of FIG. 6 illustrates these search reference end points within a sagittal tomographic image. In FIG. 6, adjacent search reference points among the search reference origin points $SO_1$ through $SO_N$ are connected by lines, resulting in the line denoted as line SO. Similarly, adjacent search reference end points from among the search reference end points $SP_{11}$ through $SP_{N1}$ and the search reference end points $SP_{12}$ through $SP_{N2}$, which are on the same sides of the search reference origin points are connected by lines, resulting in bent lines $SP_1$ and $SP_2$. A shape model that defines a reference coordinate system for extracting the abdominal cavity region, represented by coordinated axes having the two bent lines $SP_1$ and $SP_2$ as axes and illustrated in the image toward the right of FIG. 6, is generated in this manner. Note that in the above description, the distances between the search reference end points are set within each axial tomographic image such that the lines that connect the search reference end points $SP_{11}$ through $SP_{N1}$ and the search reference end points $SP_{12}$ through $SP_{N2}$ are bent lines. Alternatively, these distances may be obtained by employing a function.

The bone boundary point detecting section 16 sets a plurality of search reference points along the search reference lines $SL_1$ through $SL_N$, sets sight lines that extend radially toward the exteriors of the search reference end points $SP_{11}$ through $SP_{N1}$ and $SP_{12}$ through $SP_{N2}$, and sets sight lines that extend in the upper and lower directions of the search reference points other than the search reference end points. Searches are conducted along each sight line toward the exterior of the subject, and the points at which contact is first made with bone regions $BR_1$ through $BR_N$ are detected as bone boundary points $BP_1$ through $BP_N$. Here, it is preferable for the sight lines to be set within each axial tomographic image such that they do not intersect with each other, from the viewpoint of processing efficiency and the positions of bone boundary points to be detected. Note that a plurality of the bone boundary points are present within each axial tomographic image. However, in order to simplify the explanation, each of the reference designations $BP_1$ through $BP_N$ denote a plurality of bone boundary points within each axial tomographic image.

Figure 7:
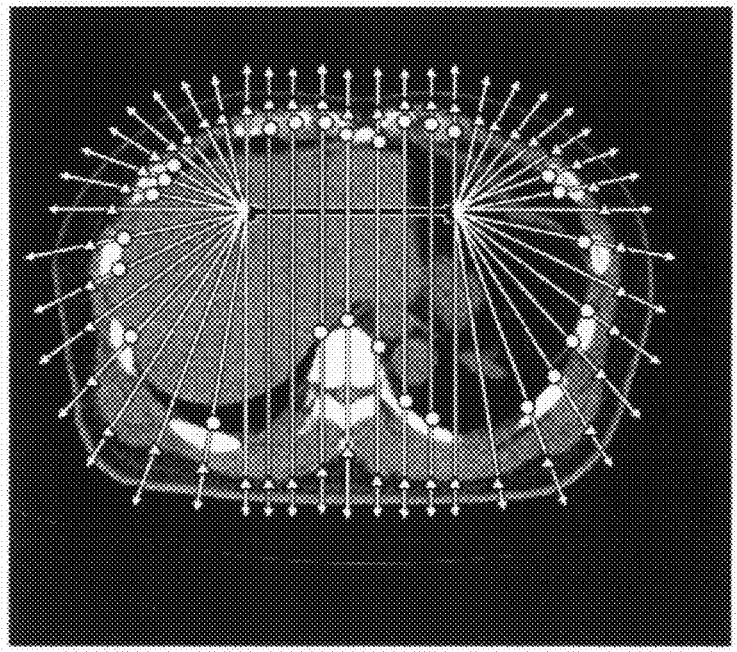
FIG. 7 is a diagram that illustrates detection examples of bone boundary points and abdominal wall muscle outline points within an axial tomographic image of the upper abdominal cavity.
Figure 8:
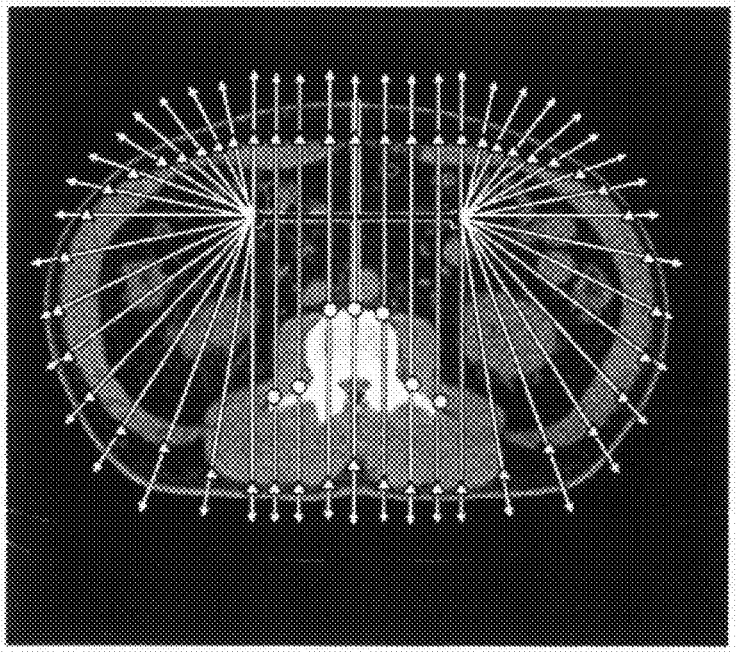
FIG. 8 is a diagram that illustrates detection examples of bone boundary points and abdominal wall muscle outline points within an axial tomographic image of the central portion of the abdominal cavity.
Figure 9:
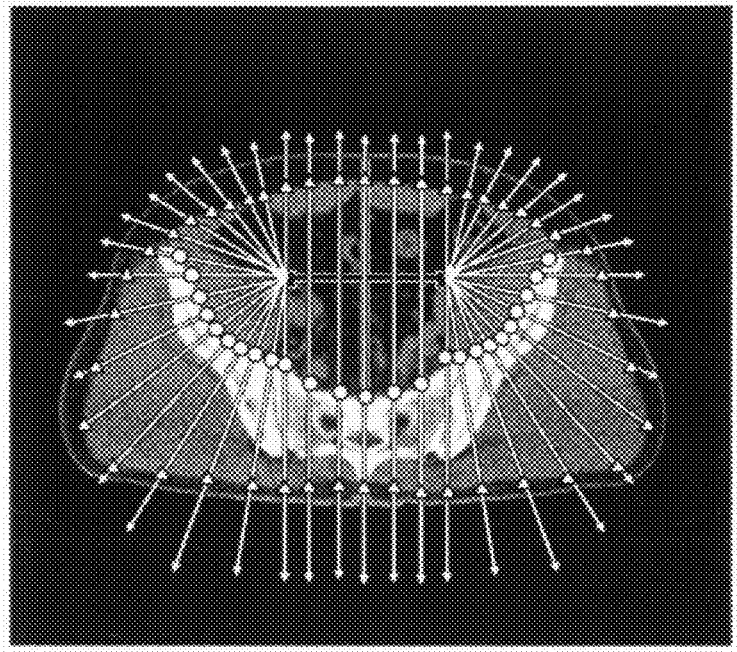
FIG. 9 is a diagram that illustrates detection examples of bone boundary points and abdominal wall muscle outline points within an axial tomographic image of a portion of the abdominal cavity beneath the fifth lumbar vertebra.
Figure 10:
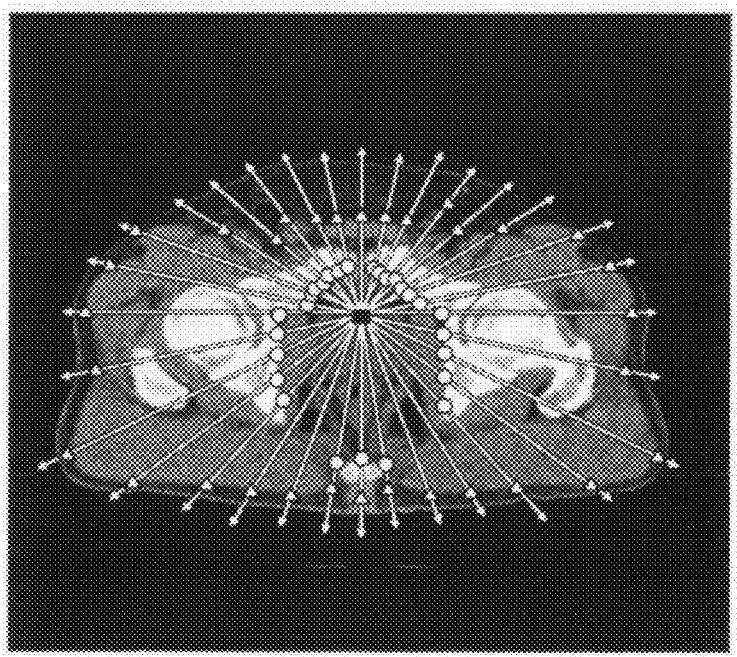
FIG. 10 is a diagram that illustrates detection examples of bone boundary points and abdominal wall muscle outline points within an axial tomographic image of the lowermost portion of the abdominal cavity.

FIG. 7 is a diagram that illustrates detection results for bone boundary points within an axial tomographic image positioned at a comparatively upward position from among the axial tomographic image $AX_1$ through $AX_N$, which are targets of processing. As illustrated in FIG. 7, boundary points with the ribs and the vertebra (the points denoted by circles in FIG. 7. the same applies hereafter) are detected. FIG. 8 is a diagram that illustrates detection results for bone boundary points within an axial tomographic image positioned at a central position from among the axial tomographic image $AX_1$ through $AX_N$, which are targets of processing. As illustrated in FIG. 8, because ribs are not present at this position, only the boundary points with the vertebrae are detected. FIG. 9 is a diagram that illustrates detection results for bone boundary points within an axial tomographic image positioned at a position comparatively lower than the fifth lumber vertebra, from among the axial tomographic images $AX_1$ through $AX_N$. As illustrated in FIG. 9, the pelvis appears in the image at this position, and therefore, a boundary point with a bone that forms the sacrum is detected. Note that because this axial tomographic image is at a slice position lower than the fifth lumbar vertebra, the distance between the search reference end points is shorter than those within FIGS. 7 and 8. FIG. 10 is a diagram that illustrates detection results for bone boundary points within the axial tomographic image $AX_N$ positioned at the lowest position from among the axial tomographic images $AX_1$ through $AX_N$. A boundary point with a bone that forms the pelvis, such as the coccyx, is detected. In addition, because the search reference endpoints are converged at the search reference origin point, the sight lines are set to extend radially 360 degrees from this point.

The abdominal wall muscle outline extracting section 17 searches from the body surface to search reference points along the search reference lines $SL_1$ through $SL_N$, along a plurality of sight lines which have been set in a manner similar to that during the processes performed by the bone boundary points detecting section 16. After points on the body surface outlines $SC_1$ through $SC_N$ extracted by the body surface outline extracting section 14 are passed through, boundary points at which regions (subcutaneous fat regions) having pixel values corresponding to fat CT values transition to regions (abdominal wall muscle regions) having pixel values corresponding to muscle CT values are detected. The boundary points which are detected along each sight line are three dimensionally interpolated, to extract outlines $AMC_1$ through $AMC_N$ that represent the outlines of the exteriors of the abdominal wall muscles. The points denoted by triangular marks within FIGS. 7 through 10 are examples of the outlines of the abdominal wall muscles detected by the process described above. Note that because the manners in which the sight lines are set by the bone boundary point detecting section 16 and the abdominal wall muscle outline extracting section 17 are the same, the setting processes for the sight lines may be incorporated into a single process. In this case, the searches from the search reference points toward the body surface may be performed to detect the bone boundary points $BP_1$ through $BP_N$, and thereafter, the searches from the body surface toward the search reference points may be performed to extract the outlines $AMC_1$ through $AMC_N$ of the abdominal wall muscles. In addition, the process for extracting the outlines $AMC_1$ through $AMC_N$ of the abdominal wall muscles is not limited to the process described above, and any known process may be employed.

The three dimensional abdominal cavity region extracting section 18 extracts a three dimensional abdominal cavity region $ACR_O$, based on the bone boundary points $BP_{11-1M}$ through $BP_{N1-NM}$, and the body surface outlines $SC_1$ through $SC_N$ within each of the axial tomographic images $AX_1$ through $AX_N$, and the curved surface DI that represents the diaphragm.

First, the three dimensional abdominal cavity region extracting section 18 performs a process that estimates an abdominal cavity candidate region $ACR_{-1}$, based on bone boundary points $BP_1$ through $BP_N$ and the body surface outlines $SC_1$ through $SC_N$ within the axial tomographic images $AX_1$ through $AX_N$. Here, a method that employs the RBF (Radial Basis Function) interpolating process will be described as a specific example of the estimating method.

RBF interpolation is a method that estimates a continuous multi dimensional insertion function that passes through discrete points assigned within an image space, of which attributes are known, as smoothly as possible.

Figure 11A:
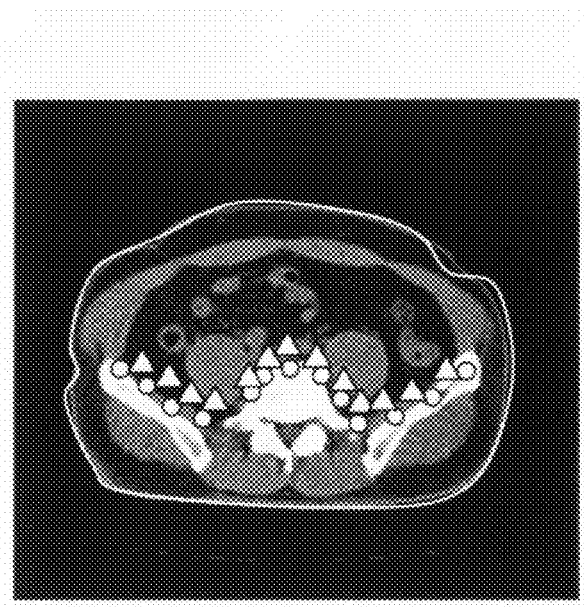
FIG. 11A is a diagram that illustrates the group of discrete points to be employed in RBF interpolation within an axial tomographic image.
Figure 11B:
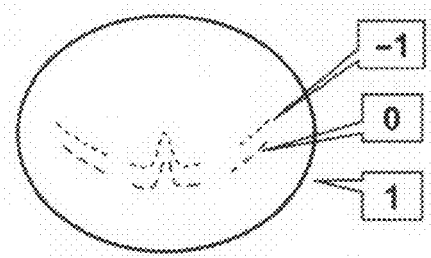
FIG. 11B is a diagram in which only the group of discrete points to be employed in RBF interpolation are extracted.

First, as illustrated in FIG. 11A, values (hereinafter, referred to as height values) of "0" for extracting the three dimensional abdominal cavity region $ACR_0$ are assigned to the positions of the bone boundary points $BP_{11-1M}$ through (indicated by circular marks) within each of the axial tomographic images $AX_1$ through $AX_N$. Height values of "1" are assigned to the positions of the body surface outlines $SC_1$ through $SC_N$ (indicated by the bold line toward the exterior). Then, height values of "−1" are assigned to positions within the abdominal cavity region (indicated by triangular marks), which are positions 1 mm to 5 mm toward the interior of the subject's body from the positions of the bone boundary points $BP_{11-1M}$ through $BP_{N1-NM}$. FIG. 11B is a diagram that represents only positions within the axial tomographic image of FIG. 11A, to which height values have been assigned.

The positions to which the height values have been assigned within all of the axial tomographic images $AX_1$ through $AX_N$ are represented by the following vector $c_i$.

$$\{\vec{c}_i = (c_i^x, c_i^y, c_i^z)\} (1 \leq i \leq n)$$

wherein $c_i^x$, $c_i^y$, and $c_i^z$ respectively represent the x coordinate value, the y coordinate value, and the z coordinate value of each of the aforementioned positions. In addition, i is a numeral for identifying each of the aforementioned positions.

Here, a function f(x) for a desired vector x is represented by Formula (1) below, employing RBF.

$$f(\vec{x}) = p(\vec{x}) + \sum_{j=1}^{n} d_j \phi(\vec{x} - \vec{c}_j) \tag{1}$$

wherein p(x) satisfies Formula (2) below.

$$p(\vec{x}) = p_0 + p_1 x + p_2 y + p_3 z \tag{2}$$

In addition, examples of a base function $\phi(x)$ include functions (3) and (4) below.

$$\phi(\vec{x}) = |\vec{x}| \tag{3}$$

$$\phi(\vec{x}) = |\vec{x}|^2 \log |\vec{x}| \tag{4}$$

Here, $\{d_i\}$ ($1 \leq i \leq n$), $p_0$, $p_1$, $p_2$ and $p_3$ that satisfy the following formulas (5) and (6) are derived.

$$\sum_{j=1}^{n} d_j = \sum_{j=1}^{n} d_j c_j^x = \sum_{j=1}^{n} d_j c_j^y = \sum_{j=1}^{n} d_j c_j^z = 0 \tag{5}$$

$$f(\vec{c}_i) = h_i = p(\vec{c}_i) + \sum_{j=1}^{n} d_j \phi(\vec{c}_i - \vec{c}_j) \tag{6}$$

wherein $\{h_i\}$ ($1 \leq i \leq n$) is the height value at each of the aforementioned positions. The function f(x) is determined by the above calculations.

Figure 11C:
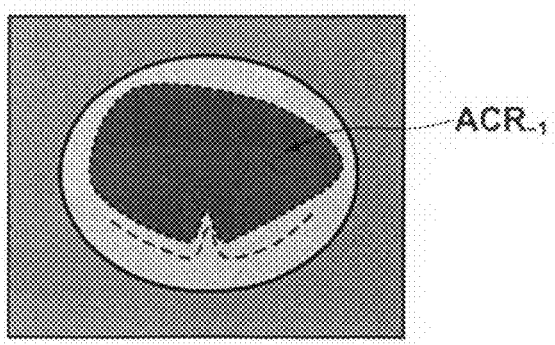
FIG. 11C is a diagram that schematically represents the results of RBF interpolation, to which multiple values have been assigned.

FIG. 11C is a diagram that schematically illustrates the results of the RBF interpolation, to which multiple values have been assigned. The region at which the height value is "−1" within the images, that is, the region where the height value is a negative value, ultimately becomes the abdominal cavity region candidate $ACR_{-1}$. Note that in the case that the RBF interpolation process is performed employing data regarding the outline of the body surface as described above, the abdominal cavity region candidate $ACR_{-1}$ will not extend outside the outline of the body surface, because the height value of the outline of the body surface is "1", and the height values of regions within the body are "1" or less.

Figure 12A:
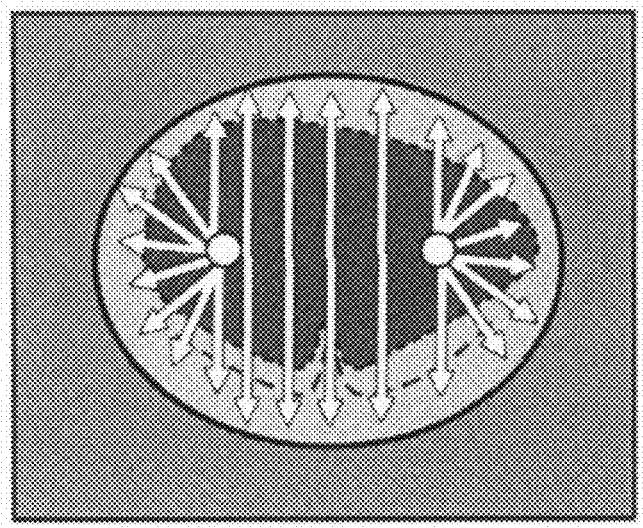
FIG. 12A is a diagram that schematically illustrates a search process for obtaining the outline of the three dimensional abdominal cavity candidate region.
Figure 12B:
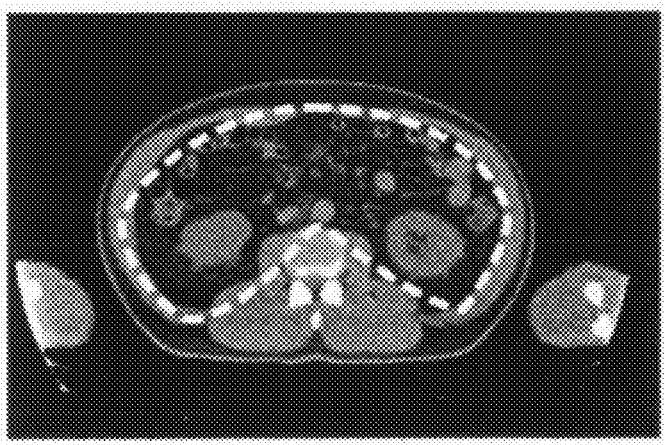
FIG. 12B is a diagram that illustrates an example of the three dimensional abdominal cavity candidate region.

Note that as illustrated in FIGS. 12A and 12B, the outline of the abdominal cavity region candidate $ACR_{-1}$ can be obtained (FIG. 12B), by setting a plurality of sigh lines similar to those illustrated in FIGS. 7 through 10 from each of the search reference lines $SL_1$ through $SL_N$, which have been set in each of the axial tomographic images $AX_1$ through $AX_N$, and by detecting the boundaries at which the height values change from "−1" to "0" by searching along each sight line from each of the search reference points (FIG. 12A).

The three dimensional abdominal cavity region extracting section 18 further obtains data regarding the curved surface DI that represents the diaphragm detected by the diaphragm detecting section 11, and determines the region of the abdominal cavity region candidate $ACR_{-1}$ beneath the curved surface DI to be the abdominal cavity region $ACR_0$.

Note that a method in which shape models of abdominal cavity region candidates obtained by statistical analysis of main component analysis are prepared in advance, and the plurality of bone boundary points $BP_1$ through $BP_N$ are fitted into the shape models may be employed to extract the abdominal cavity region candidate $ACR_{-1}$. In addition, the main component analysis may be performed by designating all bones as a single bone, or by grouping the bones into specific bone groups. Further, the shape models may be shape models that represent surfaces, density value distribution models, etc.

The three dimensional abdominal cavity region correcting section 19 first judges whether the abdominal cavity region $ACR_0$ extracted by the three dimensional abdominal cavity region extracting section 18 includes any portions that extend outside the outlines $AMC_1$ through $AMC_N$ of the exteriors of the abdominal wall muscles, that is, whether the abdominal cavity region $ACR_0$ includes portions between the body surface and the outlines of the abdominal wall surfaces. In the case that such portions are present, the abdominal cavity region $ACR_0$ is corrected such that all portions thereof are toward the interior of the outlines $AMC_1$ through $AMC_N$ of the exteriors of the abdominal wall muscles. Specifically, searches are conducted again along each of the sight lines set by the bone boundary point detecting section 16, to judge whether intersections of the sight lines and the outline of the abdominal cavity region $ACR_0$ are present toward the exterior of the outlines $AMC_1$ through $AMC_N$ of the exteriors of the abdominal wall muscles. In the case that such intersections are present, searches are conducted toward the search reference points along the sight lines on which the intersections exist, and boundary points with regions at which pixel values transition to those corresponding to fat Cr values (visceral fat regions) after passing through regions having pixel values corresponding to fat CT values (subcutaneous fat regions) and regions having pixel values corresponding to muscle CT values (abdominal wall muscle regions) are detected. Then, correction is performed such that the positions of the detected boundary points are designated as the outline points of the abdominal cavity region. This correction is effective in cases that subjects have a great amount of subcutaneous fat toward the front side of the abdomen.

Further, the three dimensional abdominal region correcting section 19 judges that outline points of the abdominal cavity region $ACR_0$ which are positioned toward the interiors of the outlines $AMC_1$ through $AMC_N$ of the abdominal wall muscles and of which the pixel values correspond to fat CT values are not correct outline points of the abdominal cavity region $ACR_0$ but are within the visceral fat region. The three dimensional abdominal region correcting section 19 searches along the set sight lines from the outline points to the body surface, and detects points at which the pixel values first fall out of the range of pixel values that correspond to fat CT values. Then, correction is performed such that the detected points are designated as the outline points of the abdominal cavity region. This correction is effective to correct shifting of outline points in the rear peritoneal membrane region (the lower left and lower right portions of FIG. 8).

The fat region extracting section 20 extracts regions having pixel values corresponding to fat CT values from each of the axial tomographic images $AX_1$ through $AX_N$ as fat regions $FR_1$ through $FR_N$.

The visceral fat region discriminating section 21 discriminates portions of the fat regions $FR_1$ through $FR_N$ present within a corrected three dimensional abdominal cavity region $ACR_1$ as visceral fat regions $VFR_1$ through $VFR_N$.

The subcutaneous fat region discriminating section 22 discriminates portions of the fat regions $FR_1$ through $FR_N$ present toward the exterior of the outlines $AMC_1$ through $AMC_N$ of the abdominal wall muscles and toward the interior of the body surface outlines $SC_1$ through $SC_N$ as subcutaneous fat regions $SFR_1$ through $SFR_N$.

Figure 13A:
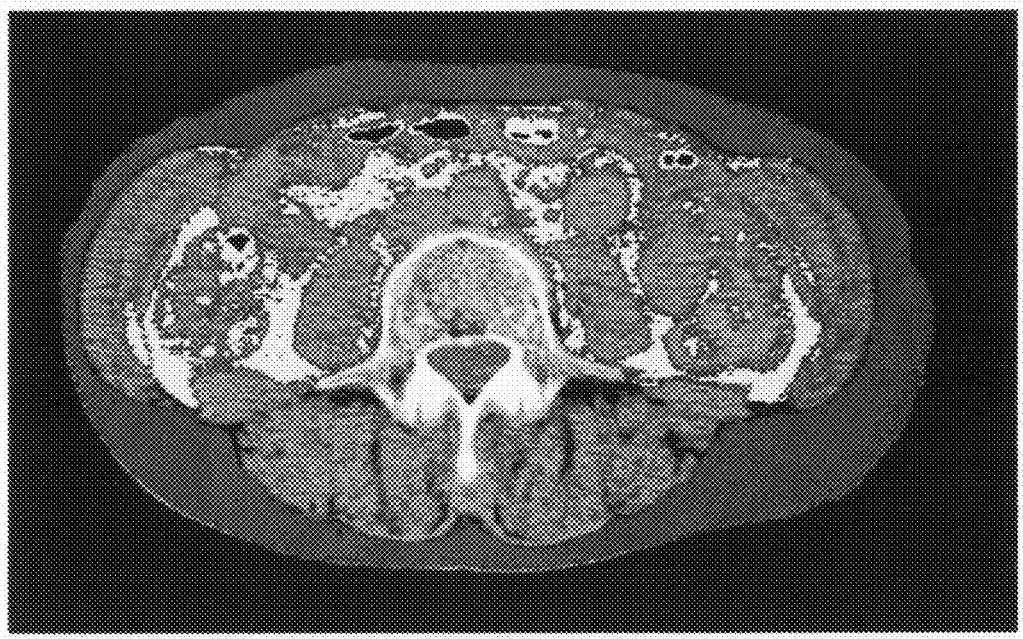
FIG. 13A is an image in which visceral fat regions and subcutaneous fat regions within an axial tomographic image are displayed in different colors.
Figure 13B:
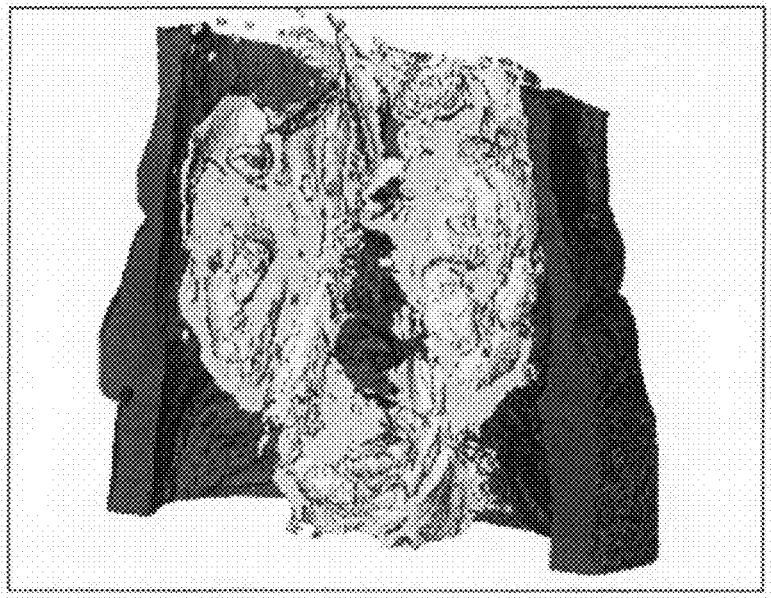
FIG. 13B is an example of an image in which visceral fat regions and subcutaneous fat regions are displayed three dimensionally in different colors.
Figure 13C:
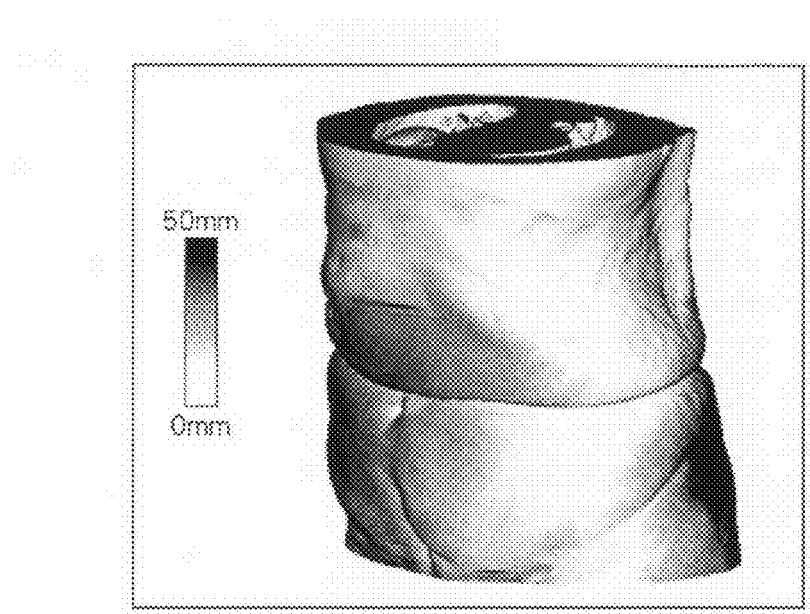
FIG. 13C is an example of an image in which the thicknesses of subcutaneous fat at different portions are mapped onto an image that represents the body surface three dimensionally.
Figure 13D:
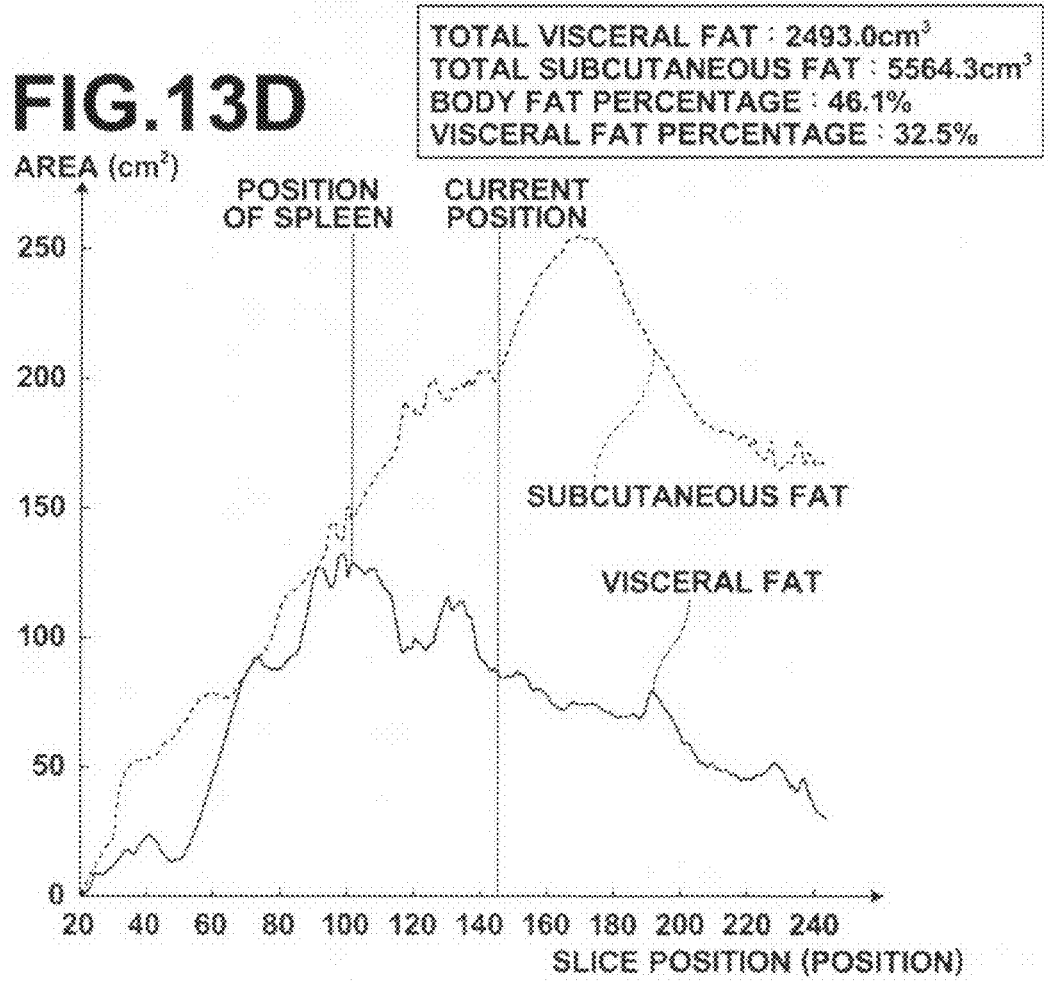
FIG. 13D is a graph that represents the amounts of visceral fat and subcutaneous fat at the slice position of each axial tomographic image.
Figure 14A:
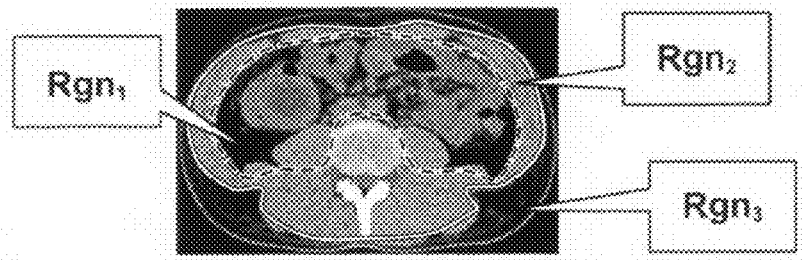
FIG. 14A is a diagram that illustrates an example of a method for classifying fat regions within an axial tomographic image.
Figure 14B:
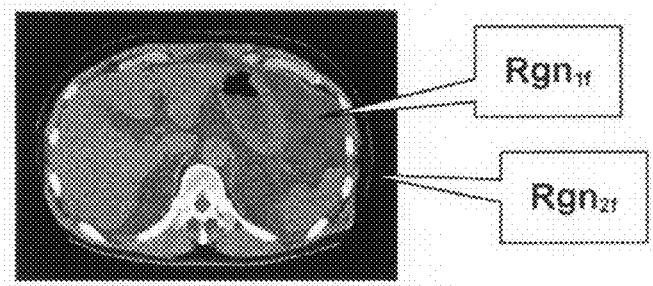
FIG. 14B is a diagram that illustrates an example of classified fat regions within an axial tomographic image in the vicinity of the upper edge of the abdominal cavity.
Figure 14C:
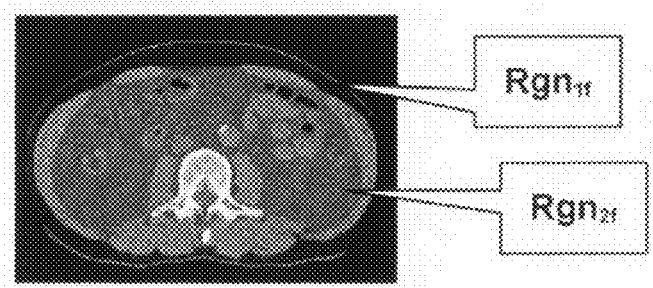
FIG. 14C is a diagram that illustrates an example of classified fat regions within an axial tomographic image in the vicinity of the central portion of the abdominal cavity.
Figure 14D:
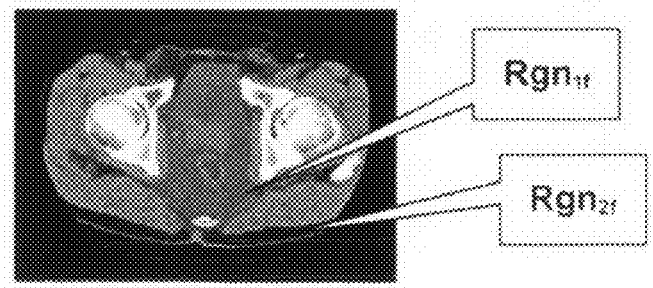
FIG. 14D is a diagram that illustrates an example of classified fat regions within an axial tomographic image in the vicinity of the lower edge of the abdominal cavity.

The three dimensional body fat measuring section 23 measures body fat (visceral fat and subcutaneous fat) based on the visceral fat regions $VFR_1$ through $VFR_N$ and the subcutaneous fat regions $SFR_1$ through $SFR_N$ within each of the axial tomographic images $AX_1$ through $AX_N$, and outputs results Rst. Specifically, the areas of the visceral fat regions $VFR_1$ through $VFR_N$ and the subcutaneous fat regions $SFR_1$ through $SFR_N$ are calculated, and the calculated areas are multiplied by slice thicknesses or slice intervals. The sums of the multiplication results for each of the visceral fat regions and the subcutaneous regions are calculated, to obtain the volume of visceral fat and the volume of subcutaneous fat. Here, the visceral fat percentage, the subcutaneous fat percentage, etc. may also be calculated. In addition, images in which the visceral fat regions are represented in a color different from that which represents subcutaneous fat regions may be generated (refer to FIG. 13A). Further, the subcutaneous fat regions and the visceral fat regions may be displayed three dimensionally in different colors, as illustrated in FIG. 13B. Still further, the thickness of each subcutaneous fat portion may be mapped onto an image that three dimensionally represents the body surface, as illustrated in FIG. 13C. Still yet further, the amounts of visceral fat and subcutaneous fat at the slice position of each axial tomographic image may be displayed as a graph, as illustrated in FIG. 13D.

The determination of the processing target data by each of the aforementioned processing sections, the order of the processes performed by each of the processing sections, etc. are controlled by a control section (not shown). The control section is realized by executing a main program of the three dimensional body fat measuring program that causes the image processing workstation to execute the three dimensional body fat measuring process. Meanwhile, each of the aforementioned processing sections are realized by the control section calling up subprograms of the three dimensional body fat measuring program. Input data and parameters to be employed by the called up processing sections are provided to the processing sections by the control section. The processing sections are configured to transmit a "process completed" message to the control section when the process to be performed by each processing section is complete. The control section controls whether the next processing step is to be performed, based on the presence/absence of these "process completed" messages.

Next, the flow of the three dimensional body fat measuring process performed by the present embodiment, that is, the details of the control exerted by the control section, will be described with reference to FIG. 2.

First, when the three dimensional body fat measuring program of the present invention is started, the control section obtains data that specify three dimensional medical image data V, which is provided as a startup parameter for the program. Then, the control section calls up the processing target range determining section 12 and the diaphragm detecting section 11, provides the data that specify the three dimensional medical image data V, and causes these sections to perform the processes assigned thereto.

After receipt of a "process completed" message from the processing target range determining section 12 is detected, the control section calls up the bone region extracting section 13, the body surface outline extracting section 14, and the fat region extracting section 20, provides these sections with data that specify the axial tomographic images $AX_1$ through $AX_N$ within the processing target range, and causes these sections to perform the processes assigned thereto.

Next, after receipt of a "process completed" message from the body surface outline extracting section 14 is detected, the control section calls up the search reference line setting section 15, provides the data that specify the axial tomographic images $AX_1$ through $AX_N$ within the processing target range and data regarding the body surface outlines $SC_1$ through $SC_N$ thereto, and causes this section to perform the processes assigned thereto.

After receipt of a "process completed" message from the search reference line setting section 15 is detected, the control section calls up the abdominal wall muscle outline extracting section 17, provides data that specify the axial tomographic images $AX_1$ through $AX_N$ within the processing target range and data regarding the search reference end points $SP_{11}$ through $SP_{N1}$ and the search reference end points $SP_{12}$ through $SP_{N2}$, and causes this section to perform the processes assigned thereto. Here, if receipt of the "process completed" message from the bone region extracting section 13 has also been detected, the bone boundary point detecting section 16 is called up, data that specify the axial tomographic images $AX_1$ through $AX_N$ within the processing target range, data regarding the search reference end points $SP_{11}$ through $SP_{N1}$ and the search reference end points $SP_{12}$ through $SP_{N2}$, and data regarding the bone regions $BR'$ through $BR_N$ are provided, and this section is caused to perform the processes assigned thereto.

When receipt of "process completed" messages from the bone boundary point detecting section 16 and the diaphragm detecting section 11 is detected, the control section calls up the three dimensional abdominal cavity region extracting section 18, provides this section with data that specify the axial tomographic images $AX_1$ through $AX_N$ within the processing target range, data regarding the bone boundary points $BP_{11-1M}$ through $BP_{N1-NM}$, data regarding the body surface outlines $SC_1$ through $SC_N$, and data DI regarding the diaphragm thereto, and causes this section to perform the processes assigned thereto.

When receipt of "process completed" messages from the three dimensional abdominal cavity region extracting section 18 and the abdominal wall muscle outline extracting section 17 is detected, the control section calls up the three dimensional abdominal cavity region correcting section 19, provides data regarding the three dimensional abdominal cavity region $ACR_0$ and the outlines $AMC_1$ through $AMC_N$ of the abdominal wall muscles thereto, and causes this section to perform the processes assigned thereto.

When receipt of a "process completed" message from the three dimensional abdominal cavity correcting section 19 is detected, the control section confirms that receipt of a "process completed" message from the fat region extracting section 20 has been detected. Then, the control section calls up the visceral fat region discriminating section 21, provides the corrected three dimensional abdominal cavity region $ACR_1$ and data regarding the fat regions $FR_1$ through $FR_N$ thereto, and causes this section to perform the processes assigned thereto. In addition, the control section calls up the subcutaneous fat region discriminating section 22, provides data regarding the body surface outlines $SC_1$ through $SC_N$, data regarding the outlines $AMC_1$ through $AMC_N$ of the abdominal wall muscles, and data regarding the fat regions $FR_1$ through $FR_N$ thereto, and causes this section to perform the processes assigned thereto. Note that the subcutaneous fat region discriminating section 22 may be called up when receipt of "process completed" messages from all of the body surface outline extracting section 14, the abdominal wall muscle outline extracting section 17, and the fat region extracting section 20 has been detected.

When receipt of "process completed" messages from the visceral fat discriminating section 21 and the subcutaneous fat discriminating section 22 is detected, the control section calls up the three dimensional body fat measuring section 23, provides data regarding the visceral fat regions $VFR_1$ through $VFR_N$ and data regarding the subcutaneous fat regions $SFR_1$ through $SFR_N$ thereto, and causes this section to perform the processes assigned thereto. When receipt of a "process completed" message from the three dimensional body fat measuring section 23 is detected, the measurement results Rst are caused to be displayed on the display of the image processing workstation 3.

According to the three dimensional body fat measuring system in which a three dimensional abdominal cavity region extracting apparatus of an embodiment of the present invention is incorporated, the bone boundary point detecting section 16 detects the plurality of bone boundary points $BP_1$ through $BP_N$ that represent the boundaries between the bone regions $BR_1$ through $BR_N$ and regions positioned toward the interiors of the bone regions $BR_1$ through $BR_N$ within the plurality of axial tomographic images $AX_1$ through $AX_N$ that represent a portion of the subject from the vicinity of the upper end of the liver to the vicinity of the pubic symphysis. The three dimensional abdominal cavity region extracting section 18 estimates curved surfaces within each of the plurality of axial tomographic images $AX_1$ through $AX_N$ that substantially contact the interiors of the detected plurality of bone boundary points $BP_1$ through $BP_N$ detected. The region surrounded by the curved surfaces is extracted as the three dimensional abdominal cavity region.

Here, the estimated curved surfaces substantially contact the interiors of the plurality of bone boundary points $BP_1$ through $BP_N$ that represent the boundaries between the bone regions $BR_1$ through $BR_N$ and regions positions toward the interiors of the bone regions $BR_1$ through $BR_N$ within the subject. Therefore, the curved surfaces are positioned toward the interior of the spinal column in the vicinity of the spinal column within the axial tomographic images $AX_1$ through $AX_N$. Accordingly, the regions between the outline of the abdominal cavity and the outer periphery of the abdominal wall muscle in the vicinity of the area behind the spinal column are outside the abdominal cavity region, and the extraction accuracy of the abdominal cavity region is improved (refer to FIG. 13A). In the case visceral fat is measured, for example, these regions are removed from the visceral fat regions, and therefore, the accuracy of fat region discrimination is improved.

In addition, the plurality of bone boundary points $BP_1$ through $BP_N$ within the plurality of axial tomographic images are utilized three dimensionally to estimate the curved surfaces to extract the three dimensional abdominal cavity region. Therefore, the estimation accuracy of the curved surfaces is higher compared to the method disclosed in Patent Document 3, in which the regions are discriminated independently for each axial tomographic image, because data regarding the bone boundary points in the axial direction of the body are also utilized. As a result, the accuracy of abdominal cavity region extraction is also improved.

Further, the diaphragm detecting section 11 extracts the diaphragm portion DI of the subject, and the three dimensional abdominal cavity region extracting section 18 extracts the region within the three dimensional image surrounded by the extracted diaphragm portion DI and the curved surfaces as the three dimensional abdominal cavity region. Therefore, the extraction accuracy with respect to the upper edge portion of the abdominal cavity is improved.

The body surface outline extracting section 14 extracts the outlines $SC_1$ through $SC_N$ of the surface of the subject's body, and the abdominal wall muscle outline extracting section 17 extracts the outlines $AMC_1$ through $AMC_N$ of the exterior of the abdominal wall muscles. The three dimensional abdominal cavity region extracting section 18 estimates the curved surfaces such that they do not extend outside the extracted outlines $SC_1$ through $SC_N$ of the surface of the subject's body. In addition, the three dimensional abdominal cavity region correcting section 19 corrects the curved surfaces such that they do not extend outside the extracted outlines $AMC_1$ through $AMC_N$ of the abdominal wall muscles. Therefore, the curved surfaces being estimated as shapes that protrude outside of these outlines in portions of the subject in the vicinity of the abdomen where no ribs or pelvis are present can be avoided. Accordingly, the accuracy of estimation of the curved surfaces in the vicinity of the abdomen is improved. As a result, accuracy of abdominal cavity region extraction is improved in the vicinity of the abdomen.

The bone boundary point detecting section 16 sets search reference lines $SL_1$ through $SL_N$ having end points at both sides of a line that bisects the subject in the horizontal direction are set at positions which are clearly anatomically in the abdominal cavity region are set within each of the plurality of axial tomographic images $AX_1$ through $AX_N$, such that the distances between the end points become shorter in axial tomographic images that represent lower portions of the subject. Then, searches are performed along a plurality of lines of sight that do not intersect and extend from a plurality of points along the search reference lines $SL_1$ through $SL_N$ toward the exterior of the subject, and points that contact the bone regions $BR_1$ through $BR_N$ first are detected as the bone boundary points $BP_1$ through $BP_N$. In this case, the initiation points of the searches include those which are shifted from the center of the subject in the horizontal direction. Therefore, it becomes possible to set the bone boundary points $BP_1$ through $BP_N$ along the interiors of the spinal column (vertebrae) positioned at the center. In addition, the search reference lines $SL_1$ through $SL_N$ are set such that the distances between the end points become shorter in axial tomographic images that represent lower portions of the subject. Therefore, the search initiation points can be set within the interior of the pelvis in axial tomographic images in the vicinity of the pelvis. This enables setting of the bone boundary points within the interior of the pelvis, which contributes to improvements in the accuracy of estimation of the curved surfaces.

Modifications to the configuration of the system, the flows of processes, and the configuration of the modules described above within a scope that does not stray from the spirit of the present invention are still included within the technical scope of the present invention. The embodiment described above is exemplary, and the description thereof is not to be utilized to interpret the technical scope of the present invention in a limiting manner.

For example, the results of the three dimensional abdominal cavity extracting process of the present invention were utilized for three dimensional body fat measurement in the embodiment described above. Alternatively, the results of the three dimensional abdominal cavity extracting process of the present invention may be employed to limit a range from which extraction is to be performed in a process for extracting organs within the abdominal cavity.

Explanation of the Reference Numerals

| | |
|---|---|
| 1 | modality |
| 2 | image storage server |
| 3 | image processing work station |
| 9 | network |
| 11 | diaphragm detecting section |

-continued

Explanation of the Reference Numerals

| | |
|---|---|
| 12 | processing range determining section |
| 13 | bone region extracting section |
| 14 | body surface outline extracting section |
| 15 | search reference line setting section |
| 16 | bone boundary point detecting section |
| 17 | abdominal wall muscle outline extracting section |
| 18 | three dimensional abdominal cavity region extracting section |
| 19 | three dimensional abdominal cavity region correcting section |
| 20 | fat region extracting section |
| 21 | visceral fat region discriminating section |
| 22 | subcutaneous fat region discriminating section |
| 23 | three dimensional body fat measuring section |

The invention claimed is:

1. A three dimensional abdominal cavity region extracting apparatus, comprising:
bone region extracting means, for extracting bone regions that represent the bones of a subject within a plurality of axial tomographic images including at least a first axial tomographic image that includes the ribs of the subject, a second axial tomographic image that includes the vicinity of the upper edge of the pelvis of the subject, and a third axial tomographic image that includes the vicinity of the pelvis of the subject lower than that which appears in the second axial tomographic image, obtained from a three dimensional image that represents a portion of the subject from the vicinity of the upper end of the liver to the vicinity of the pubic symphysis;
bone boundary point detecting means, for detecting a plurality of bone boundary points that represent the boundaries between the detected bone regions and regions positioned toward the interiors of the bone regions within the plurality of axial tomographic images; and
abdominal cavity region extracting means, for estimating curved surfaces within the three dimensional image that substantially contact the interiors of the plurality of bone boundary points detected in each of the plurality of axial tomographic images, based on the bone boundary points, and for extracting a three dimensional abdominal region surrounded by the curved surfaces as a three dimensional abdominal cavity region.

2. A three dimensional abdominal cavity region extracting apparatus as defined in claim 1, further comprising:
diaphragm extracting means, for extracting diaphragm portions from at least one of the plurality of axial tomographic images and a plurality of axial tomographic images obtained from a three dimensional image that represents the thoracic region of the subject; wherein:
the abdominal cavity region extracting means extracts a region from within the three dimensional image surrounded by the curved surfaces and having the extracted diaphragm portions as the upper edge thereof as the three dimensional abdominal cavity region.

3. A three dimensional abdominal cavity region extracting apparatus as defined in claim 1, further comprising:
body surface outline extracting means, for extracting the outline of the surface of the body of the subject from each of the plurality of axial tomographic images; wherein:
the abdominal cavity region extracting means estimates the curved surfaces such that the curved surfaces do not extend outside the exterior of the surface of the body.

4. A three dimensional abdominal cavity region extracting apparatus as defined in claim 1, further comprising:
abdominal wall muscle outline extracting means, for extracting the outline of the exterior of the abdominal wall muscles of the subject from within each of the plurality of axial tomographic images; wherein:
the abdominal cavity region extracting means estimates the curved surfaces such that the curved surfaces do not extend outside the outline of the exterior of the abdominal wall muscles.

5. A three dimensional abdominal cavity region extracting apparatus as defined in claim 1, further comprising:
visceral fat region discriminating means, for discriminating regions having pixel values that correspond to fat of the subject within the three dimensional abdominal cavity region extracted by the abdominal cavity region extracting means as three dimensional visceral fat regions.

6. A three dimensional abdominal cavity region extracting apparatus as defined in claim 1, further comprising:
subcutaneous fat region discriminating means, for discriminating three dimensional subcutaneous fat regions within the three dimensional image, by discriminating subcutaneous fat regions that represent subcutaneous fat of the subject from within each of the plurality of axial tomographic images.

7. A three dimensional abdominal cavity region extracting apparatus as defined in claim 1, wherein:
the bone boundary point detecting means sets search reference lines having end points at both sides of a line that bisects the subject in the horizontal direction at positions which are clearly anatomically in the abdominal cavity region within each of the plurality of axial tomographic images, such that the distances between the end points become shorter in axial tomographic images that represent lower portions of the subject, searches along a plurality of lines of sight that do not intersect and extend from a plurality of points along the search reference lines toward the exterior of the subject, and detects points that contact the bone regions first as the bone boundary points.

8. A three dimensional abdominal cavity region extracting method, comprising the steps of:
extracting bone regions that represent the bones of a subject within a plurality of axial tomographic images including at least a first axial tomographic image that includes the ribs of the subject, a second axial tomographic image that includes the vicinity of the upper edge of the pelvis of the subject, and a third axial tomographic image that includes the vicinity of the pelvis of the subject lower than that which appears in the second axial tomographic image, obtained from a three dimensional image that represents a portion of the subject from the vicinity of the upper end of the liver to the vicinity of the pubic symphysis;
detecting a plurality of bone boundary points that represent the boundaries between the detected bone regions and regions positioned toward the interiors of the bone regions within the plurality of axial tomographic images; and
estimating curved surfaces within the three dimensional image that substantially contact the interiors of the plurality of bone boundary points detected in each of the plurality of axial tomographic images, based on the bone boundary points; and
extracting a three dimensional abdominal region surrounded by the curved surfaces.

9. A non-transitory computer readable medium having stored therein a program that causes a computer to execute the procedures of:
extracting bone regions that represent the bones of a subject within a plurality of axial tomographic images including at least a first axial tomographic image that includes the ribs of the subject, a second axial tomographic image that includes the vicinity of the upper edge of the pelvis of the subject, and a third axial tomographic image that includes the vicinity of the pelvis of the subject lower than that which appears in the second axial tomographic image, obtained from a three dimensional image that represents a portion of the subject from the vicinity of the upper end of the liver to the vicinity of the pubic symphysis;
detecting a plurality of bone boundary points that represent the boundaries between the detected bone regions and regions positioned toward the interiors of the bone regions within the plurality of axial tomographic images; and
estimating curved surfaces within the three dimensional image that substantially contact the interiors of the plurality of bone boundary points detected in each of the plurality of axial tomographic images, based on the bone boundary points; and
extracting a three dimensional abdominal region surrounded by the curved surfaces.

10. A three dimensional abdominal cavity region extracting apparatus as defined in claim 1, wherein:
the first axial tomographic image is an image that represents the vicinity of the upper edge of the liver of the subject.

11. A three dimensional abdominal cavity region extracting apparatus as defined in claim 1, wherein:
the third axial tomographic image is an image that represents the vicinity of the pubic symphysis of the subject.

* * * * *